(12) United States Patent
Scheibel et al.

(10) Patent No.: US 8,372,436 B2
(45) Date of Patent: Feb. 12, 2013

(54) METHODS OF PRODUCING NANO-AND MICROCAPSULES OF SPIDER SILK PROTEINS

(75) Inventors: Thomas Scheibel, Bayreuth (DE); Daniel Huemmerich, Frankenthal (DE); Andreas Bausch, Unterschleiβheim (DE); Kevin Hermanson, Cincinnati, OH (US)

(73) Assignee: Amsik GmbH, Munich (DE)

( * ) Notice: Subject to any disclaimer, the term of this patent is extended or adjusted under 35 U.S.C. 154(b) by 703 days.

(21) Appl. No.: 11/989,907

(22) PCT Filed: Aug. 1, 2006

(86) PCT No.: PCT/EP2006/007608
§ 371 (c)(1),
(2), (4) Date: Nov. 13, 2009

(87) PCT Pub. No.: WO2007/014755
PCT Pub. Date: Feb. 8, 2007

(65) Prior Publication Data
US 2010/0056438 A1    Mar. 4, 2010

(30) Foreign Application Priority Data
Aug. 1, 2005   (EP) .................................... 05016712

(51) Int. Cl.
*A61K 9/50*    (2006.01)
*A61K 38/17*   (2006.01)

(52) U.S. Cl. ........................................ 424/490; 530/353

(58) Field of Classification Search .................. None
See application file for complete search history.

(56) References Cited

U.S. PATENT DOCUMENTS

| | | | |
|---|---|---|---|
| 6,268,169 B1 | 7/2001 | Fahnestock | |
| 6,280,747 B1 | 8/2001 | Philippe et al. | |
| 6,303,150 B1 | 10/2001 | Perrier et al. | |
| 6,608,242 B1 | 8/2003 | Yang | |
| 6,841,162 B2 * | 1/2005 | Philippe et al. | 424/401 |
| 2002/0064539 A1 | 5/2002 | Philippe et al. | |
| 2003/0165548 A1 | 9/2003 | Tsubouchi | |
| 2008/0085272 A1 | 4/2008 | Kaplan et al. | |

FOREIGN PATENT DOCUMENTS

| | | |
|---|---|---|
| EP | 823 258 | 2/1998 |
| EP | 1 459 728 | 9/2004 |
| JP | 8-268905 | 10/1996 |
| JP | 8-295697 | 11/1996 |
| JP | 10-251299 | 9/1998 |
| WO | WO94/29450 | 12/1994 |
| WO | WO01/42300 | 6/2001 |
| WO | WO01/90389 | 11/2001 |
| WO | WO2004/044172 | 5/2004 |
| WO | WO 2005/123114 A | 12/2005 |

OTHER PUBLICATIONS

Jin et al., "Mechanism of silk processing in insects and spiders", Nature, vol. 424, pp. 1057-1061.*
Huemmerich et al., "Primary Structure Elements of Spider Dragline Silks and Their Contribution to Protein Solubility", Biochemistry, 2004, 43:13604-13612.*
Hermanson et al., "Engineered Microcapsules Fabricated from Reconstituted Spider Silk", Advanced Materials, 2007, 19:1810-1815.*
Altman, G.H., et al., "Silk-based biomaterials," Biomaterials, vol. 24, No. 3 pp. 401-416 (2003).
Altman, G.H., et al., "Silk matrix for tissue 1-13 engineered anterior cruciate ligaments," Biomaterials, vol. 23, No. 20 pp. 4131-4141 (2002).
European Search Report corresponding to European Application No. 05016712.1 dated Nov. 29, 2005.
International Search Report corresponding to International Application No. PCT/EP2006/007608 dated Jul. 12, 2006.
Megeed, Z. et al., "In vitro and in vivo evaluation of recombinant silk-elastinlike hydrogels for cancer gene therapy," Journal of Controlled Release, vol. 94, No. 2-3 pp. 433-445 (2004).
Wang, L., et al., "Microstructure and gelation behavior of hydroxyapatite-based nanocomposite sol containing chemically modified silk fibroin," Colloids and Surfaces, vol. 254, No. 1-3 pp. 159-164 (2005).

* cited by examiner

*Primary Examiner* — Suzanne M Noakes
(74) *Attorney, Agent, or Firm* — Faegre Baker Daniels LLP

(57) ABSTRACT

The present invention is directed to a method of producing nano- and microcapsules from spider silk proteins The invention is further directed to nano- or microcapsules obtainable by this method as well as pharmaceutical, cosmetical and food compositions containing same.

20 Claims, 16 Drawing Sheets

*(a)*

(b)

SEQUENCE LISTING

<160> NUMBER OF SEQ ID NOS: 55

<210> SEQ ID NO 1
<211> LENGTH: 653
<212> TYPE: PRT
<213> ORGANISM: Araneus diadematus

<400> SEQUENCE: 1

```
Met Ala Ser Met Thr Gly Gly Gln Gln Met Gly Arg Asp Pro Asn Ser
1               5                   10                  15

Ala Arg Ala Gly Ser Gly Gln Gln Gly Pro Gly Gln Gln Gly Pro Gly
            20                  25                  30

Gln Gln Gly Pro Gly Gln Gln Gly Pro Tyr Gly Pro Gly Ala Ser Ala
        35                  40                  45

Ala Ala Ala Ala Ala Gly Gly Tyr Gly Pro Gly Ser Gly Gln Gln Gly
    50                  55                  60

Pro Ser Gln Gln Gly Pro Gly Gln Gln Gly Pro Gly Gly Gln Gly Pro
65                  70                  75                  80

Tyr Gly Pro Gly Ala Ser Ala Ala Ala Ala Ala Gly Gly Tyr Gly
                85                  90                  95

Pro Gly Ser Gly Gln Gln Gly Pro Gly Gly Gln Gly Pro Tyr Gly Pro
            100                 105                 110

Gly Ser Ser Ala Ala Ala Ala Ala Gly Gly Asn Gly Pro Gly Ser
        115                 120                 125

Gly Gln Gln Gly Pro Gly Gln Gln Gly Pro Gly Gln Gln Gly Pro Gly
    130                 135                 140

Ala Ser Ala Ala Ala Ala Ala Gly Gly Tyr Gly Pro Gly Ser Gly
145                 150                 155                 160
```

-continued

Gln Gln Gly Pro Gly Gln Gln Gly Pro Gly Gln Gly Pro Tyr Gly
                165                 170                 175

Pro Gly Ala Ser Ala Ala Ala Ala Ala Gly Gly Tyr Gly Pro Gly
                180                 185                 190

Ser Gly Gln Gln Gly Pro Gly Gln Gln Gly Pro Gly Gln Gly Pro
                195                 200                 205

Tyr Gly Pro Gly Ala Ser Ala Ala Ala Ala Gly Gly Tyr Gly
    210                 215                 220

Pro Gly Ser Gly Gln Gln Gly Pro Gly Gln Gln Gly Pro Gly Gln Gln
225                 230                 235                 240

Gly Pro Gly Gly Gln Gly Pro Tyr Gly Pro Gly Ala Ser Ala Ala Ala
                245                 250                 255

Ala Ala Ala Gly Gly Tyr Gly Pro Gly Tyr Gly Gln Gln Gly Pro Gly
                260                 265                 270

Gln Gln Gly Pro Gly Gly Gln Gly Pro Tyr Gly Pro Gly Ala Ser Ala
                275                 280                 285

Ala Ser Ala Ala Ser Gly Gly Tyr Gly Pro Gly Ser Gly Gln Gln Gly
                290                 295                 300

Pro Gly Gln Gln Gly Pro Gly Gln Gly Pro Tyr Gly Pro Gly Ala
305                 310                 315                 320

Ser Ala Ala Ala Ala Ala Gly Gly Tyr Gly Pro Gly Ser Gly Gln
                325                 330                 335

Gln Gly Pro Gly Gln Gln Gly Pro Gly Gln Gln Gly Pro Gly Gln Gln
                340                 345                 350

Gly Pro Gly Gly Gln Gly Pro Tyr Gly Pro Gly Ala Ser Ala Ala Ala
                355                 360                 365

Ala Ala Ala Gly Gly Tyr Gly Pro Gly Ser Gly Gln Gln Gly Pro Gly
                370                 375                 380

Gln Gln Gly Pro Gly Gln Gln Gly Pro Gly Gln Gln Gly Pro Gly Gln
385                 390                 395                 400

Gln Gly Pro Gly Gln Gln Gly Pro Gly Gln Gln Gly Pro Gly Gln Gln
                405                 410                 415

Gly Pro Gly Gln Gln Gly Pro Gly Gly Gln Gly Ala Tyr Gly Pro Gly
                420                 425                 430

Ala Ser Ala Ala Ala Gly Ala Ala Gly Tyr Gly Pro Gly Ser Gly
                435                 440                 445

Gln Gln Gly Pro Gly Gln Gln Gly Pro Gly Gln Gln Gly Pro Gly Gln
                450                 455                 460

Gln Gly Pro Gly Gln Gln Gly Pro Gly Gln Gln Gly Pro Gly Gln Gln
465                 470                 475                 480

Gly Pro Gly Gln Gln Gly Pro Tyr Gly Pro Gly Ala Ser Ala Ala Ala
                485                 490                 495

Ala Ala Ala Gly Gly Tyr Gly Pro Gly Ser Gly Gln Gln Gly Pro Gly
                500                 505                 510

Gln Gln Gly Pro Gly Gln Gln Gly Pro Val Gly Gln Gly Pro Tyr Gly
                515                 520                 525

Pro Gly Ala Ala Ser Ala Ala Val Ser Val Gly Gly Tyr Gly Pro Gln
                530                 535                 540

Ser Ser Ser Ala Pro Val Ala Ser Ala Ala Ser Arg Leu Ser Ser
545                 550                 555                 560

Pro Ala Ala Ser Ser Arg Val Ser Ser Ala Val Ser Ser Leu Val Ser
                565                 570                 575

Ser Gly Pro Thr Asn Gln Ala Ala Leu Ser Asn Thr Ile Ser Ser Val
                580                 585                 590

```
Val Ser Gln Val Ser Ala Ser Asn Pro Gly Leu Ser Gly Cys Asp Val
            595                 600                 605

Leu Val Gln Ala Leu Leu Glu Val Val Ser Ala Leu Val Ser Ile Leu
    610                 615                 620

Gly Ser Ser Ile Gly Gln Ile Asn Tyr Gly Ala Ser Ala Gln Tyr
625                 630                 635                 640

Thr Gln Met Val Gly Gln Ser Val Ala Gln Ala Leu Ala
                645                 650

<210> SEQ ID NO 2
<211> LENGTH: 671
<212> TYPE: PRT
<213> ORGANISM: Araneus diadematus

<400> SEQUENCE: 2

Met Ala Ser Met Thr Gly Gly Gln Gln Met Gly Arg Ala Ala Arg Ala
1               5                   10                  15

Gly Ser Ser Ala Ala Ala Ala Ala Ala Ser Gly Ser Gly Gly Tyr
            20                  25                  30

Gly Pro Glu Asn Gln Gly Pro Ser Gly Pro Val Ala Tyr Gly Pro Gly
            35                  40                  45

Gly Pro Val Ser Ser Ala Ala Ala Ala Ala Ala Gly Ser Gly Pro
        50                  55                  60

Gly Gly Tyr Gly Pro Glu Asn Gln Gly Pro Ser Gly Pro Gly Gly Tyr
65                  70                  75                  80

Gly Pro Gly Gly Ser Gly Ser Ser Ala Ala Ala Ala Ala Ala Ala
                85                  90                  95

Ser Gly Pro Gly Gly Tyr Gly Pro Gly Ser Gln Gly Pro Ser Gly Pro
            100                 105                 110

Gly Gly Ser Gly Gly Tyr Gly Pro Gly Ser Gln Gly Pro Ser Gly Pro
            115                 120                 125

Gly Ala Ser Ala Ala Ala Ala Ala Ala Ser Gly Pro Gly
            130                 135                 140

Gly Tyr Gly Pro Gly Ser Gln Gly Pro Ser Gly Pro Gly Ala Tyr Gly
145                 150                 155                 160

Pro Gly Gly Pro Gly Ser Ser Ala Ala Ala Ser Gly Pro Gly Gly Tyr
                165                 170                 175

Gly Pro Gly Ser Gln Gly Pro Ser Gly Pro Gly Gly Ser Gly Gly Tyr
            180                 185                 190

Gly Pro Gly Ser Gln Gly Pro Ser Gly Pro Gly Gly Pro Gly Ala Ser
            195                 200                 205

Ala Ala Ala Ala Ala Ala Ala Ser Gly Pro Gly Gly Tyr Gly
210                 215                 220

Pro Gly Ser Gln Gly Pro Ser Gly Pro Gly Ala Tyr Gly Pro Gly Gly
225                 230                 235                 240

Pro Gly Ser Ser Ala Ala Ala Ser Gly Pro Gly Gly Tyr Gly Pro Gly
                245                 250                 255

Ser Gln Gly Pro Ser Gly Pro Gly Ala Tyr Gly Pro Gly Pro Gly
            260                 265                 270

Ser Ser Ala Ala Ala Ala Ala Ala Gly Ser Gly Pro Gly Gly Tyr
            275                 280                 285

Gly Pro Gly Asn Gln Gly Pro Ser Gly Pro Gly Gly Tyr Gly Pro Gly
            290                 295                 300

Gly Pro Gly Ser Ser Ala Ala Ala Ala Ala Ala Ser Gly Pro Gly
305                 310                 315                 320
```

Gly Tyr Gly Pro Gly Ser Gln Gly Pro Ser Gly Pro Gly Val Tyr Gly
            325                 330                 335

Pro Gly Gly Pro Gly Ser Ser Ala Ala Ala Ala Ala Ala Ala Gly Ser
            340                 345                 350

Gly Pro Gly Gly Tyr Gly Pro Gly Asn Gln Gly Pro Ser Gly Pro Gly
            355                 360                 365

Gly Tyr Gly Pro Gly Gly Ser Gly Ser Ser Ala Ala Ala Ala Ala Ala
            370                 375                 380

Ala Ala Ser Gly Pro Gly Gly Tyr Gly Pro Gly Ser Gln Gly Pro Ser
385                 390                 395                 400

Gly Pro Gly Gly Ser Gly Gly Tyr Gly Pro Gly Ser Gln Gly Pro Ser
                405                 410                 415

Gly Pro Gly Ala Ser Ser Ala Ala Ala Ala Ala Ala Ala Ser Gly
            420                 425                 430

Pro Gly Gly Tyr Gly Pro Gly Ser Gln Gly Pro Ser Gly Pro Gly Ala
            435                 440                 445

Tyr Gly Pro Gly Gly Pro Gly Ser Ser Ala Ala Ala Ser Gly Pro Gly
            450                 455                 460

Gly Tyr Gly Pro Gly Ser Gln Gly Pro Ser Gly Pro Gly Ala Tyr Gly
465                 470                 475                 480

Pro Gly Gly Pro Gly Ser Ser Ala Ala Ala Ala Ala Ala Ala Ser Gly
                485                 490                 495

Pro Gly Gly Tyr Gly Pro Gly Ser Gln Gly Pro Ser Gly Pro Gly Gly
            500                 505                 510

Ser Arg Gly Tyr Gly Pro Gly Ser Gln Gly Pro Gly Gly Pro Gly Ala
            515                 520                 525

Ser Ala Ala Ala Ala Ala Ala Ala Ser Gly Pro Gly Gly Tyr
            530                 535                 540

Gly Pro Gly Ser Gln Gly Pro Ser Gly Pro Gly Tyr Gln Gly Pro Ser
545                 550                 555                 560

Gly Pro Gly Ala Tyr Gly Pro Ser Pro Ser Ala Ser Ala Ser Val Ala
                565                 570                 575

Ala Ser Arg Leu Ser Ser Pro Ala Ala Ser Ser Arg Val Ser Ser Ala
            580                 585                 590

Val Ser Ser Leu Val Ser Gly Pro Thr Asn Gly Ala Ala Val Ser
            595                 600                 605

Gly Ala Leu Asn Ser Leu Val Ser Gln Ile Ser Ala Ser Asn Pro Gly
            610                 615                 620

Leu Ser Gly Cys Asp Ala Leu Val Gln Ala Leu Leu Glu Leu Val Ser
625                 630                 635                 640

Ala Leu Val Ala Ile Leu Ser Ser Ala Ser Ile Gly Gln Val Asn Val
                645                 650                 655

Ser Ser Val Ser Gln Ser Thr Gln Met Ile Ser Gln Ala Leu Ser
            660                 665                 670

<210> SEQ ID NO 3
<211> LENGTH: 24
<212> TYPE: PRT
<213> ORGANISM: Artificial Sequence
<220> FEATURE:
<223> OTHER INFORMATION: Artificially synthesized Module A (ADF-3)

<400> SEQUENCE: 3

Gly Pro Tyr Gly Pro Gly Ala Ser Ala Ala Ala Ala Ala Gly Gly
1               5                   10                  15

Tyr Gly Pro Gly Ser Gly Gln Gln
            20

<210> SEQ ID NO 4
<211> LENGTH: 20
<212> TYPE: PRT
<213> ORGANISM: Artificial Sequence
<220> FEATURE:
<223> OTHER INFORMATION: Artificially synthesized Module Q (ADF-3)

<400> SEQUENCE: 4

Gly Pro Gly Gln Gln Gly Pro Gly Gln Gln Gly Pro Gly Gln Gln Gly
1               5                   10                  15

Pro Gly Gln Gln
            20

<210> SEQ ID NO 5
<211> LENGTH: 35
<212> TYPE: PRT
<213> ORGANISM: Artificial Sequence
<220> FEATURE:
<223> OTHER INFORMATION: Artificially synthesized Module C (ADF-4)

<400> SEQUENCE: 5

Gly Ser Ser Ala Ala Ala Ala Ala Ala Ala Ala Ser Gly Pro Gly Gly
1               5                   10                  15

Tyr Gly Pro Glu Asn Gln Gly Pro Ser Gly Pro Gly Tyr Gly Pro
            20                  25                  30

Gly Gly Pro
        35

<210> SEQ ID NO 6
<211> LENGTH: 942
<212> TYPE: PRT
<213> ORGANISM: Nephila clavipes

<400> SEQUENCE: 6

Ala Cys Phe Thr Ser Ala Val Ile Phe Leu Phe Leu Ala Gln Cys Ala
1               5                   10                  15

Ser Thr Tyr Gly Arg Gly Ile Ile Ala Asn Ser Pro Phe Ser Asn Pro
            20                  25                  30

Asn Thr Ala Glu Ala Phe Ala Arg Ser Phe Val Ser Asn Ile Val Ser
        35                  40                  45

Ser Gly Glu Phe Gly Ala Gln Gly Ala Glu Asp Phe Asp Asp Ile Ile
    50                  55                  60

Gln Ser Leu Ile Gln Ala Gln Ser Met Gly Lys Gly Arg His Asp Thr
65                  70                  75                  80

Lys Ala Lys Ala Lys Ala Met Gln Val Ala Leu Ala Ser Ser Ile Ala
                85                  90                  95

Glu Leu Val Ile Ala Glu Ser Ser Gly Gly Asp Val Gln Arg Lys Thr
            100                 105                 110

Asn Val Ile Ser Asn Ala Leu Arg Asn Ala Leu Met Ser Thr Thr Gly
        115                 120                 125

Ser Pro Asn Glu Glu Phe Val His Glu Val Gln Asp Leu Ile Gln Met
    130                 135                 140

Leu Ser Gln Glu Gln Ile Asn Glu Val Asp Thr Ser Gly Pro Gly Gln
145                 150                 155                 160

Tyr Tyr Arg Ser Ser Ser Gly Gly Gly Gly Gly Gln Gly Gly
                165                 170                 175

Pro Val Val Thr Glu Thr Leu Thr Val Thr Val Gly Gly Ser Gly Gly

```
                180                 185                 190
Gly Gln Pro Ser Gly Ala Gly Pro Ser Gly Thr Gly Gly Tyr Ala Pro
            195                 200                 205

Thr Gly Tyr Ala Pro Ser Gly Ser Gly Ala Gly Gly Val Arg Pro Ser
210                 215                 220

Ala Ser Gly Pro Ser Gly Ser Gly Pro Ser Gly Gly Ser Arg Pro Ser
225                 230                 235                 240

Ser Ser Gly Pro Ser Gly Thr Arg Pro Ser Pro Asn Gly Ala Ser Gly
            245                 250                 255

Ser Ser Pro Gly Gly Ile Ala Pro Gly Gly Ser Asn Ser Gly Gly Ala
            260                 265                 270

Gly Val Ser Gly Ala Thr Gly Gly Pro Ala Ser Ser Gly Ser Tyr Gly
            275                 280                 285

Pro Gly Ser Thr Gly Gly Thr Tyr Gly Pro Ser Gly Gly Ser Glu Pro
            290                 295                 300

Phe Gly Pro Gly Val Ala Gly Gly Pro Tyr Ser Pro Gly Gly Ala Gly
305                 310                 315                 320

Pro Gly Gly Ala Gly Gly Ala Tyr Gly Pro Gly Gly Val Gly Thr Gly
                325                 330                 335

Gly Ala Gly Pro Gly Gly Tyr Gly Pro Gly Gly Ala Gly Pro Gly Gly
            340                 345                 350

Tyr Gly Pro Gly Gly Ala Gly Pro Gly Gly Tyr Gly Pro Gly Gly Ala
            355                 360                 365

Gly Pro Gly Gly Tyr Gly Pro Gly Gly Ala Gly Pro Gly Gly Tyr Gly
            370                 375                 380

Pro Gly Gly Ala Gly Pro Gly Gly Tyr Gly Pro Gly Gly Ala Gly Pro
385                 390                 395                 400

Gly Gly Tyr Gly Pro Gly Gly Thr Gly Pro Gly Gly Tyr Gly Pro Gly
                405                 410                 415

Gly Thr Gly Pro Gly Gly Val Gly Pro Gly Gly Ala Gly Pro Gly Gly
            420                 425                 430

Tyr Gly Pro Gly Gly Ala Gly Pro Gly Gly Ala Gly Pro Gly Gly Ala
            435                 440                 445

Gly Pro Gly Gly Ala Gly Pro Gly Gly Ala Gly Pro Gly Gly Ala Gly
            450                 455                 460

Pro Gly Gly Tyr Gly Pro Gly Ser Gly Pro Gly Gly Ala Gly Pro
465                 470                 475                 480

Ser Gly Ala Gly Leu Gly Gly Ala Gly Pro Gly Gly Ala Gly Leu Gly
                485                 490                 495

Gly Ala Gly Pro Gly Gly Ala Gly Thr Ser Gly Ala Gly Pro Gly Gly
            500                 505                 510

Ala Gly Pro Gly Gly Ala Gly Gln Gly Asp Ala Gly Pro Gly Gly Ala
            515                 520                 525

Gly Arg Gly Gly Ala Gly Arg Gly Gly Val Gly Arg Gly Gly Ala Gly
            530                 535                 540

Arg Gly Gly Ala Gly Arg Gly Gly Ala Arg Gly Gly Ala Gly Ala Gly
545                 550                 555                 560

Gly Ala Gly Gly Ala Gly Gly Ser Gly Gly Thr Thr Ile Val Glu Asp
                565                 570                 575

Leu Asp Ile Thr Ile Asp Gly Ala Asp Gly Pro Ile Thr Ile Ser Glu
            580                 585                 590

Glu Leu Thr Ile Gly Gly Ala Gly Ala Gly Gly Ser Gly Pro Gly Gly
            595                 600                 605
```

-continued

Ala Gly Pro Gly Asn Val Gly Pro Gly Arg Ser Gly Pro Gly Gly Val
610             615                 620

Gly Pro Gly Gly Ser Gly Pro Gly Gly Val Gly Pro Gly Ser Phe Gly
625             630                 635                 640

Pro Gly Gly Val Gly Pro Gly Gly Ser Gly Pro Gly Gly Val Gly Ser
            645                 650                 655

Gly Gly Ser Gly Gln Gly Gly Val Arg Pro Ser Gly Ser Gly Pro Gly
            660                 665                 670

Gly Val Gly Thr Gly Gly Val Gly Pro Gly Gly Ala Gly Gly Pro Tyr
            675                 680                 685

Gly Pro Gly Gly Ser Gly Pro Gly Gly Ala Gly Ser Ala Gly Gly Thr
690                 695                 700

Tyr Gly Pro Gly Gly Phe Gly Pro Gly Gly Phe Gly Gly Pro Gly
705                 710                 715                 720

Gly Ala Gly Gly Pro Tyr Gly Pro Gly Gly Ala Gly Pro Tyr Gly
            725                 730                 735

Pro Gly Gly Ala Gly Gly Pro Tyr Gly Pro Gly Gly Ala Gly Gly Pro
            740                 745                 750

Tyr Gly Pro Gly Gly Ala Gly Pro Tyr Gly Pro Gly Gly Ala Gly
            755                 760                 765

Gly Ser Tyr Gly Leu Gly Gly Ala Gly Gly Ser Gly Gly Val Gly Pro
            770                 775                 780

Gly Gly Ser Gly Pro Gly Gly Tyr Gly Pro Gly Gly Ala Gly Pro Gly
785                 790                 795                 800

Gly Tyr Gly Pro Gly Gly Ser Gly Pro Gly Gly Tyr Gly Pro Gly Gly
            805                 810                 815

Ser Gly Ser Gly Gly Tyr Gly Pro Gly Gly Ser Gly Pro Gly Gly Ser
            820                 825                 830

Gly Pro Gly Gly Tyr Gly Pro Gly Gly Thr Gly Pro Gly Gly Ser Glu
            835                 840                 845

Ser Gly Gly Tyr Gly Pro Gly Gly Ser Gly Pro Gly Gly Ser Gly Pro
850                 855                 860

Gly Gly Ser Gly Pro Gly Gly Ser Gly Pro Gly Gly Tyr Gly Pro Gly
865                 870                 875                 880

Gly Ser Gly Pro Ser Ser Phe Val Pro Gly Ser Gly Pro Gly Gly
            885                 890                 895

Ser Gly Pro Gly Gly Ala Gly Pro Gly Gly Ala Gly Pro Gly Gly Val
            900                 905                 910

Gly Leu Gly Gly Ala Gly Arg Gly Gly Ala Gly Arg Gly Gly Ala Gly
            915                 920                 925

Ser Val Gly Ala Gly Arg Gly Gly Ala Gly Arg Gly Gly Thr
930                 935                 940

<210> SEQ ID NO 7
<211> LENGTH: 907
<212> TYPE: PRT
<213> ORGANISM: Nephila clavipes

<400> SEQUENCE: 7

Gly Pro Gly Gly Val Gly Pro Gly Gly Ser Gly Pro Gly Gly Tyr Gly
1               5                   10                  15

Pro Gly Gly Ala Gly Pro Gly Gly Tyr Gly Pro Gly Gly Ser Gly Pro
            20                  25                  30

Gly Gly Tyr Gly Pro Gly Gly Ser Gly Pro Gly Gly Tyr Gly Pro Gly
            35                  40                  45

```
Gly Ser Gly Pro Gly Gly Tyr Gly Pro Gly Gly Ser Gly Pro Gly Gly
        50                  55                  60
Tyr Gly Pro Gly Gly Ser Gly Pro Gly Gly Tyr Gly Pro Gly Gly Tyr
 65                  70                  75                  80
Gly Pro Gly Gly Ser Gly Pro Gly Gly Tyr Gly Pro Gly Gly Thr Gly
                     85                  90                  95
Pro Gly Gly Ser Gly Pro Gly Gly Tyr Gly Pro Gly Gly Ser Gly Pro
            100                 105                 110
Gly Gly Ser Gly Pro Gly Gly Tyr Gly Pro Gly Gly Ser Gly Pro Gly
        115                 120                 125
Gly Phe Gly Pro Gly Gly Ser Gly Pro Gly Gly Tyr Gly Pro Gly Gly
    130                 135                 140
Ser Gly Pro Gly Gly Ala Gly Pro Gly Gly Val Gly Pro Gly Gly Phe
145                 150                 155                 160
Gly Pro Gly Gly Ala Gly Pro Gly Gly Ala Gly Pro Gly Gly Ala Gly
                165                 170                 175
Pro Gly Gly Ala Gly Pro Gly Gly Ala Gly Pro Gly Gly Ala Gly Pro
            180                 185                 190
Gly Gly Ala Gly Pro Gly Gly Ala Gly Pro Gly Gly Ala Gly Pro Gly
        195                 200                 205
Gly Ala Gly Pro Gly Gly Ala Gly Gly Ala Gly Ala Gly Gly Ala
    210                 215                 220
Gly Gly Ser Gly Gly Ala Gly Ser Gly Gly Thr Thr Ile Ile Glu
225                 230                 235                 240
Asp Leu Asp Ile Thr Ile Asp Gly Ala Asp Gly Pro Ile Thr Ile Ser
                245                 250                 255
Glu Glu Leu Thr Ile Ser Gly Ala Gly Gly Ser Gly Pro Gly Gly Ala
            260                 265                 270
Gly Pro Gly Gly Val Gly Pro Gly Gly Ser Gly Pro Gly Gly Val Gly
        275                 280                 285
Pro Gly Gly Ser Gly Pro Gly Gly Val Gly Pro Gly Gly Ser Gly Pro
    290                 295                 300
Gly Gly Val Gly Pro Gly Gly Ala Gly Pro Gly Gly Tyr Gly Pro Gly Gly
305                 310                 315                 320
Ser Gly Pro Gly Gly Ala Gly Gly Ala Gly Pro Gly Gly Ala Tyr
                325                 330                 335
Gly Pro Gly Gly Ser Tyr Gly Pro Gly Gly Ser Gly Pro Gly Gly
            340                 345                 350
Ala Gly Gly Pro Tyr Gly Pro Gly Gly Glu Gly Pro Gly Gly Ala Gly
        355                 360                 365
Gly Pro Tyr Gly Pro Gly Gly Ala Gly Pro Tyr Gly Pro Gly Gly
    370                 375                 380
Ala Gly Gly Pro Tyr Gly Pro Gly Gly Glu Gly Gly Pro Tyr Gly Pro
385                 390                 395                 400
Gly Gly Ser Tyr Gly Pro Gly Gly Ala Gly Pro Tyr Gly Pro Gly
                405                 410                 415
Gly Pro Tyr Gly Pro Gly Gly Glu Gly Pro Gly Gly Ala Gly Gly Pro
            420                 425                 430
Tyr Gly Pro Gly Gly Val Gly Pro Gly Gly Ser Gly Pro Gly Gly Tyr
        435                 440                 445
Gly Pro Gly Gly Ser Gly Pro Gly Gly Tyr Gly Pro Gly Gly Ala Gly
    450                 455                 460
Pro Gly Gly Tyr Gly Pro Gly Gly Ser Gly Pro Gly Gly Tyr Gly Pro
465                 470                 475                 480
```

```
                              -continued

Gly Gly Ser Gly Pro Gly Gly Tyr Gly Pro Gly Gly Ser Pro Gly
                485                 490                 495

Gly Tyr Gly Pro Gly Gly Ser Gly Pro Gly Gly Tyr Gly Ser Gly Gly
        500                 505                 510

Ala Gly Pro Gly Gly Tyr Gly Pro Gly Gly Ser Gly Pro Gly Gly Tyr
            515                 520                 525

Gly Pro Gly Gly Ser Gly Pro Gly Gly Tyr Gly Pro Gly Gly Thr Gly
        530                 535                 540

Pro Gly Gly Thr Gly Pro Gly Gly Ser Gly Pro Gly Gly Tyr Gly Pro
545                 550                 555                 560

Gly Gly Ser Gly Pro Gly Gly Ser Gly Pro Gly Gly Ser Gly Pro Gly
                565                 570                 575

Gly Tyr Gly Pro Ser Gly Ser Gly Pro Gly Gly Tyr Gly Pro Ser Gly
        580                 585                 590

Ser Gly Pro Gly Gly Tyr Gly Pro Gly Gly Ser Gly Pro Gly Gly Tyr
        595                 600                 605

Gly Pro Gly Gly Ser Gly Ala Gly Gly Thr Gly Pro Gly Gly Ala Gly
        610                 615                 620

Gly Ala Gly Gly Ala Gly Gly Ser Gly Gly Ala Gly Gly Ser Gly Gly
625                 630                 635                 640

Ala Gly Gly Ser Gly Gly Ala Gly Gly Ser Gly Gly Val Gly Gly Ser
                645                 650                 655

Gly Gly Thr Thr Ile Thr Glu Asp Leu Asp Ile Thr Ile Asp Gly Ala
                660                 665                 670

Asp Gly Pro Ile Thr Ile Ser Glu Glu Leu Thr Ile Ser Gly Ala Gly
        675                 680                 685

Gly Ser Gly Pro Gly Gly Ala Gly Pro Gly Gly Val Gly Pro Gly Gly
        690                 695                 700

Ser Gly Pro Gly Gly Val Gly Pro Gly Val Ser Gly Pro Gly Gly Val
705                 710                 715                 720

Gly Pro Gly Gly Ser Gly Pro Gly Gly Val Gly Ser Gly Gly Ser Gly
                725                 730                 735

Pro Gly Gly Val Gly Pro Gly Gly Tyr Gly Pro Gly Gly Ser Gly Ser
                740                 745                 750

Gly Gly Val Gly Pro Gly Gly Tyr Gly Pro Gly Gly Ser Gly Gly Phe
                755                 760                 765

Tyr Gly Pro Gly Gly Ser Glu Gly Pro Tyr Gly Pro Ser Gly Thr Tyr
        770                 775                 780

Gly Ser Gly Gly Gly Tyr Gly Pro Gly Gly Ala Gly Gly Pro Tyr Gly
785                 790                 795                 800

Pro Gly Ser Pro Gly Gly Ala Tyr Gly Pro Gly Ser Pro Gly Gly Ala
                805                 810                 815

Tyr Tyr Pro Ser Ser Arg Val Pro Asp Met Val Asn Gly Ile Met Ser
                820                 825                 830

Ala Met Gln Gly Ser Gly Phe Asn Tyr Gln Met Phe Gly Asn Met Leu
            835                 840                 845

Ser Gln Tyr Ser Ser Gly Ser Gly Thr Cys Asn Pro Asn Asn Val Asn
        850                 855                 860

Val Leu Met Asp Ala Leu Leu Ala Ala Leu His Cys Leu Ser Asn His
865                 870                 875                 880

Gly Ser Ser Ser Phe Ala Pro Ser Pro Thr Pro Ala Ala Met Ser Ala
                885                 890                 895

Tyr Ser Asn Ser Val Gly Arg Met Phe Ala Tyr
```

<210> SEQ ID NO 8
<211> LENGTH: 636
<212> TYPE: PRT
<213> ORGANISM: Araneus diadematus

<400> SEQUENCE: 8

Ala Arg Ala Gly Ser Gly Gln Gln Gly Pro Gly Gln Gln Gly Pro Gly
1               5                   10                  15

Gln Gln Gly Pro Gly Gln Gln Gly Pro Tyr Gly Pro Gly Ala Ser Ala
            20                  25                  30

Ala Ala Ala Ala Ala Gly Gly Tyr Gly Pro Gly Ser Gly Gln Gln Gly
        35                  40                  45

Pro Ser Gln Gln Gly Pro Gly Gln Gln Gly Pro Gly Gln Gly Pro
    50                  55                  60

Tyr Gly Pro Gly Ala Ser Ala Ala Ala Ala Ala Gly Gly Tyr Gly
65                  70                  75                  80

Pro Gly Ser Gly Gln Gln Gly Pro Gly Gln Gly Pro Tyr Gly Pro
                85                  90                  95

Gly Ser Ser Ala Ala Ala Ala Ala Gly Gly Asn Gly Pro Gly Ser
                100                 105                 110

Gly Gln Gln Gly Ala Gly Gln Gly Pro Gly Gln Gln Gly Pro Gly
            115                 120                 125

Ala Ser Ala Ala Ala Ala Ala Gly Gly Tyr Gly Pro Gly Ser Gly
    130                 135                 140

Gln Gln Gly Pro Gly Gln Gly Pro Gly Gln Gly Pro Tyr Gly
145                 150                 155                 160

Pro Gly Ala Ser Ala Ala Ala Ala Ala Gly Gly Tyr Gly Pro Gly
                165                 170                 175

Ser Gly Gln Gly Pro Gly Gln Gln Gly Pro Gly Gln Gln Gly Pro Tyr
                180                 185                 190

Gly Pro Gly Ala Ser Ala Ala Ala Ala Ala Gly Gly Tyr Gly Pro
            195                 200                 205

Gly Ser Gly Gln Gln Gly Pro Gly Gln Gln Gly Pro Gly Gln Gln Gly
    210                 215                 220

Pro Gly Gln Gly Pro Tyr Gly Pro Gly Ala Ser Ala Ala Ala Ala
225                 230                 235                 240

Ala Ala Gly Gly Tyr Gly Pro Gly Tyr Gly Gln Gln Gly Pro Gly Gln
                245                 250                 255

Gln Gly Pro Gly Gly Gln Gly Pro Tyr Gly Pro Gly Ala Ser Ala Ala
            260                 265                 270

Ser Ala Ala Ser Gly Gly Tyr Gly Pro Gly Ser Gly Gln Gln Gly Pro
        275                 280                 285

Gly Gln Gln Gly Pro Gly Gln Gly Pro Tyr Gly Pro Gly Ala Ser
    290                 295                 300

Ala Ala Ala Ala Ala Ala Gly Gly Tyr Gly Pro Gly Ser Gly Gln Gln
305                 310                 315                 320

Gly Pro Gly Gln Gln Gly Pro Gly Gln Gln Gly Pro Gly Gln Gln Gly
            325                 330                 335

Pro Gly Gly Gln Gly Pro Tyr Gly Pro Gly Ala Ser Ala Ala Ala Ala
        340                 345                 350

Ala Ala Gly Gly Tyr Gly Pro Gly Ser Gly Gln Gln Gly Pro Gly Gln
    355                 360                 365

Gln Gly Pro Gly Gln Gln Gly Pro Gly Gln Gln Gly Pro Gly Gln Gln

```
                370             375             380
Gly Pro Gly Gln Gln Gly Pro Gly Gln Gln Gly Pro Gly Gln Gln Gly
385                 390             395                 400

Pro Gly Gln Gln Gly Pro Gly Gln Gly Ala Tyr Gly Pro Gly Ala
                405                 410                 415

Ser Ala Ala Ala Gly Ala Ala Gly Gly Tyr Gly Pro Gly Ser Gly Gln
                420                 425                 430

Gln Gly Pro Gly Gln Gln Gly Pro Gly Gln Gln Gly Pro Gly Gln Gln
                435                 440                 445

Gly Pro Gly Gln Gln Gly Pro Gly Gln Gln Gly Pro Gly Gln Gln Gly
                450                 455                 460

Pro Gly Gln Gln Gly Pro Tyr Gly Pro Gly Ala Ser Ala Ala Ala Ala
465                 470                 475                 480

Ala Ala Gly Gly Tyr Gly Pro Gly Ser Gly Gln Gln Gly Pro Gly Gln
                485                 490                 495

Gln Gly Pro Gly Gln Gln Gly Pro Gly Gln Gly Pro Tyr Gly Pro
                500                 505                 510

Gly Ala Ala Ser Ala Ala Val Ser Val Gly Gly Tyr Gly Pro Gln Ser
                515                 520                 525

Ser Ser Val Pro Val Ala Ser Ala Val Ala Ser Arg Leu Ser Ser Pro
                530                 535                 540

Ala Ala Ser Ser Arg Val Ser Ser Ala Val Ser Ser Leu Val Ser Ser
545                 550                 555                 560

Gly Pro Thr Lys His Ala Ala Leu Ser Asn Thr Ile Ser Ser Val Val
                565                 570                 575

Ser Gln Val Ser Ala Ser Asn Pro Gly Leu Ser Gly Cys Asp Val Leu
                580                 585                 590

Val Gln Ala Leu Leu Glu Val Val Ser Ala Leu Val Ser Ile Leu Gly
                595                 600                 605

Ser Ser Ser Ile Gly Gln Ile Asn Tyr Gly Ala Ser Ala Gln Tyr Thr
                610                 615                 620

Gln Met Val Gly Gln Ser Val Ala Gln Ala Leu Ala
625                 630                 635

<210> SEQ ID NO 9
<211> LENGTH: 410
<212> TYPE: PRT
<213> ORGANISM: Araneus diadematus

<400> SEQUENCE: 9

Ala Gly Ser Ser Ala Ala Ala Ala Ala Ala Ser Gly Ser Gly Gly
1               5                   10                  15

Tyr Gly Pro Glu Asn Gln Gly Pro Ser Gly Pro Val Ala Tyr Gly Pro
                20                  25                  30

Gly Gly Pro Val Ser Ser Ala Ala Ala Ala Ala Ala Gly Ser Gly
                35                  40                  45

Pro Gly Gly Tyr Gly Pro Glu Asn Gln Gly Pro Ser Gly Pro Gly Gly
                50                  55                  60

Tyr Gly Pro Gly Gly Ser Gly Ser Ser Ala Ala Ala Ala Ala Ala
65                  70                  75                  80

Ala Ser Gly Pro Gly Gly Tyr Gly Pro Gly Ser Gln Gly Pro Ser Gly
                85                  90                  95

Pro Gly Gly Ser Gly Gly Tyr Gly Pro Gly Ser Gln Gly Ala Ser Gly
                100                 105                 110

Pro Gly Gly Pro Gly Ala Ser Ala Ala Ala Ala Ala Ala Ala Ala
```

```
                115                 120                 125
Ala Ser Gly Pro Gly Tyr Gly Pro Gly Ser Gln Gly Pro Ser Gly
        130                 135                 140

Pro Gly Ala Tyr Gly Pro Gly Pro Gly Ser Ser Ala Ala Ala Ala
145                 150                 155                 160

Ala Ala Ala Ala Ser Gly Pro Gly Tyr Gly Pro Gly Ser Gln Gly
                165                 170                 175

Pro Ser Gly Pro Gly Val Tyr Gly Pro Gly Pro Gly Ser Ser Ala
                180                 185                 190

Ala Ala Ala Ala Ala Gly Ser Gly Pro Gly Gly Tyr Gly Pro Glu
            195                 200                 205

Asn Gln Gly Pro Ser Gly Pro Gly Tyr Gly Pro Gly Gly Ser Gly
        210                 215                 220

Ser Ser Ala Ala Ala Ala Ala Ala Ala Ser Gly Pro Gly Gly Tyr
225                 230                 235                 240

Gly Pro Gly Ser Gln Gly Pro Ser Gly Pro Gly Gly Ser Gly Gly Tyr
                245                 250                 255

Gly Pro Gly Ser Gln Gly Gly Ser Gly Pro Gly Ala Ser Ala Ala Ala
                260                 265                 270

Ala Ala Ala Ala Ala Ser Gly Pro Gly Gly Tyr Gly Pro Gly Ser Gln
            275                 280                 285

Gly Pro Ser Gly Pro Gly Tyr Gln Gly Pro Ser Gly Pro Gly Ala Tyr
        290                 295                 300

Gly Pro Ser Pro Ser Ala Ser Ala Ser Val Ala Ala Ser Val Tyr Leu
305                 310                 315                 320

Arg Leu Gln Pro Arg Leu Glu Val Ser Ser Ala Val Ser Ser Leu Val
                325                 330                 335

Ser Ser Gly Pro Thr Asn Gly Ala Ala Val Ser Gly Ala Leu Asn Ser
                340                 345                 350

Leu Val Ser Gln Ile Ser Ala Ser Asn Pro Gly Leu Ser Gly Cys Asp
            355                 360                 365

Ala Leu Val Gln Ala Leu Leu Glu Leu Val Ser Ala Leu Val Ala Ile
        370                 375                 380

Leu Ser Ser Ala Ser Ile Gly Gln Val Asn Val Ser Ser Val Ser Gln
385                 390                 395                 400

Ser Thr Gln Met Ile Ser Gln Ala Leu Ser
                405                 410

<210> SEQ ID NO 10
<211> LENGTH: 140
<212> TYPE: PRT
<213> ORGANISM: Artificial Sequence
<220> FEATURE:
<223> OTHER INFORMATION: Artificially synthesized NR3 (ADF-3)

<400> SEQUENCE: 10

Met Ala Ser Met Thr Gly Gly Gln Gln Met Gly Arg Gly Ser Met Gly
1               5                   10                  15

Ala Ala Ser Ala Ala Val Ser Val Gly Gly Tyr Gly Pro Gln Ser Ser
            20                  25                  30

Ser Ala Pro Val Ala Ser Ala Ala Ala Ser Arg Leu Ser Ser Pro Ala
        35                  40                  45

Ala Ser Ser Arg Val Ser Ser Ala Val Ser Ser Leu Val Ser Ser Gly
    50                  55                  60

Pro Thr Asn Gln Ala Ala Leu Ser Asn Thr Ile Ser Ser Val Val Ser
65                  70                  75                  80
```

```
Gln Val Ser Ala Ser Asn Pro Gly Leu Ser Gly Cys Asp Val Leu Val
                85                  90                  95

Gln Ala Leu Leu Glu Val Val Ser Ala Leu Val Ser Ile Leu Gly Ser
            100                 105                 110

Ser Ser Ile Gly Gln Ile Asn Tyr Gly Ala Ser Ala Gln Tyr Thr Gln
        115                 120                 125

Met Val Gly Gln Ser Val Ala Gln Ala Leu Ala Gly
    130                 135                 140

<210> SEQ ID NO 11
<211> LENGTH: 125
<212> TYPE: PRT
<213> ORGANISM: Artificial Sequence
<220> FEATURE:
<223> OTHER INFORMATION: Artificially synthesized NR4 (ADF-4)

<400> SEQUENCE: 11

Met Ala Ser Met Thr Gly Gly Gln Gln Met Gly Arg Gly Ser Met Gly
1               5                   10                  15

Ala Tyr Gly Pro Ser Pro Ser Ala Ser Ala Ser Val Ala Ala Ser Arg
            20                  25                  30

Leu Ser Ser Pro Ala Ala Ser Ser Arg Val Ser Ser Ala Val Ser Ser
        35                  40                  45

Leu Val Ser Ser Gly Pro Thr Asn Gly Ala Ala Val Ser Gly Ala Leu
    50                  55                  60

Asn Ser Leu Val Ser Gln Ile Ser Ala Ser Asn Pro Gly Leu Ser Gly
65                  70                  75                  80

Cys Asp Ala Leu Val Gln Ala Leu Leu Glu Leu Val Ser Ala Leu Val
                85                  90                  95

Ala Ile Leu Ser Ser Ala Ser Ile Gly Gln Val Asn Val Ser Ser Val
            100                 105                 110

Ser Gln Ser Thr Gln Met Ile Ser Gln Ala Leu Ser Gly
        115                 120                 125

<210> SEQ ID NO 12
<211> LENGTH: 1959
<212> TYPE: DNA
<213> ORGANISM: Araneus diadematus

<400> SEQUENCE: 12
atggctagca tgactggtgg acagcaaatg ggtcgggatc cgaattcggc acgagccgga      60
tctggacaac aaggacccgg acaacaagga cccggacaac aaggacccgg acaacaagga     120
ccatatggac ccgtgcatc cgccgcagca gcagccgctg gaggttatgg acccggatct     180
ggacaacaag gacccagcca acaaggacct ggccaacaag acccggtgg tcaaggacca     240 tatggacccg tgcatccgc cgccgcagca gccgctggtg gatatggacc cggttccgga     300
caacaaggac caggaggtca aggaccatat ggacctggtt catccgctgc cgcagcagcc     360
gctggaggta atgggcccgg atctggacaa caagggcccg gtcaacaagg tcctggacaa     420
caaggacccg gtgcatccgc cgccgcagca gccgctggag gatacggacc cggatctgga     480
caacaaggac ccggacaaca aggaccagga ggtcaaggac catatggacc tggtgcatcc     540
gccgctgcag cagccgctgg aggatacgga cccggatctg acaacaagg accaggacaa     600 caaggaccag gaggtcaagg accatatgga cccggtgcat ccgctgcagc agcagccgct     660
ggaggttatg gacccggatc tggacaacaa ggacccggac aacaaggacc tggacaacaa     720
ggacccggtg gtcaaggacc atatggaccc ggtgcatccg ccgccgcagc agccgctgga     780
```

```
ggatacggac ccggttatgg acagcaagga ccaggacaac aaggaccagg aggtcaagga      840
ccatatggac ctggtgcatc cgccgcctca gcagcctctg gaggatacgg acccggatct      900
ggacaacaag gacccggaca caaggacct ggaggtcaag gaccatatgg acctggtgca       960
tccgccgcag cagcagccgc tggaggttat ggacccggat ctggacaaca aggaccaggc     1020
caacaaggac ccgtcaaca aggacctgga caacaaggac ccgtggtca aggaccatat       1080 ggacctggtg catccgccgc agcagcagcc gctggaggtt atggacccgg atctggacaa     1140
caaggacccg tcaacaagg acccggtcaa caaggacccg tcaacaagg acccggtcaa       1200 caaggacccg gccaacaagg acccggtcaa caaggacccg gccaacaagg acctggtcaa     1260
caaggtcccg gtggtcaagg gcatatggga cctggtgcat ccgccgcagc aggagccgct     1320
ggaggttatg gacccggatc tggacaacaa ggacccggac aacaaggacc cggacaacaa     1380
ggacccggac aacaaggacc cggacaacaa ggacccggac aacaaggacc cggacaacaa     1440
ggacccggac aacaaggacc atatggacct ggtgcatccg ccgcagcagc agccgctgga     1500
ggttatggac ccggatctgg acaacaagga cccggccaac aaggacctgg acaacaagga     1560
cccgttggtc aaggaccata tggacctggt gcggcttctg cagctgtatc tgttggagga     1620
tatggaccac aaagctcctc ggctcctgtt gcatcagcag ccgcttctcg cctttcttct     1680
ccagcggcca gttctagagt ttcatcggct gtatcatctt tggtatctag tggacctact     1740
aatcaagctg cactttctaa tactatcagt agcgttgtat cgcaagttag tgcaagtaat     1800
cctggtcttt ctgttgcga tgtacttgtg caagcattgc tcgaagttgt atcggccctg     1860
gtatctatcc ttggatcttc tagtatcggg caaattaact atggtgcctc tgctcagtac     1920
acccaaatgg taggtcaatc tgtagctcaa gcccttgct                             1959

<210> SEQ ID NO 13
<211> LENGTH: 2013
<212> TYPE: DNA
<213> ORGANISM: Araneus diadematus

<400> SEQUENCE: 13
atggctagca tgactggtgg acagcaaatg ggtcgcgcgg cacgagcagg atcttcagca       60
gcagcggccg cggcagcaag tggatctgga ggatacggac ctgaaaaacca aggaccatct     120 ggacctgtag catatggacc tggtggaccc gtatcttcag ctgcagcagc agccgctgca      180
ggaagtggac ctggtggata cggacctgaa aaccaaggac catctggacc cggaggatat      240
ggacctggtg gttccggatc ttcagcagca gcagcagccg ctgcagcaag tggacctgga      300
ggatatggac ctggaagcca aggaccatct ggacctggtg gatccggagg atatggtccc      360
ggaagccaag ggccatctgg acctggtgca tcttcggcag cagcagcagc cgctgcagca      420
agtggacctg gaggatatgg acctggaagc caaggaccat ctggacctgg agcatatgga      480
cctggtggac ccgatcttca gctgcagca agtggacctg gaggatatgg acctggaagc      540
caaggaccat ctggacctgg tgatccgga ggatatggtc ccggaagcca agggccatct       600
ggacctggtg ggcctggtgc atctgcggca gcagcagcag ccgctgcagc aagtggacct      660
ggaggatatg gacctggaag ccaaggacca tctggacctg gagcatatgg acctggtgga      720 cccgatctt cagctgcagc aagtggacct ggaggatatg gacctggaag ccaaggacca      780
tctggacctg gagcatatgg acctggtgga cccggatctt cagctgcagc agcagccgct     840
gcaggaagtg gacctggtgg atacggacct ggaaaccaag gaccatctgg acccggagga     900
tatggacctg gtggtcccgg atcttcagca gcagcagccg ctgcagcaag tggacctgga     960
```

```
ggatatggac ctggaagcca aggaccatct ggacctggag tatatggacc tggtggaccc    1020
ggatcttcag ctgcagcagc agccgctgca ggaagtggac ctggtggata cggacctgga    1080
aaccaaggac catctggacc cggaggatat ggacctggtg gttccggatc ttcagcagca    1140
gcagcagccg ctgcagcaag tggacctgga ggatatggac ctggaagcca aggaccatct    1200
ggacctggtg gatccggagg atatggtccc ggaagccaag gccatctgg  acctggtgca    1260 tcttcggcag cagcagcagc cgctgcagca agtggacctg gaggatatgg acctggaagc    1320
caaggaccat ctggacctgg agcatatgga cctggtggac ccggatcttc agctgcagca    1380
agtggacctg gaggatatgg acctggaagc caaggaccat ctggtcctgg agcatatgga    1440
cctggtggac ccggatcttc agctgcagca gccgctgcag caagtggacc tggaggatat    1500
ggacctggaa gccaaggacc atctggacct ggtggatccc gaggatatgg tcccggaagc    1560
caaggacctg gtgggcctgg agcatctgcg gcagcagcag cagccgctgc agcaagtgga    1620
cctggaggat atggacctgg aagccaagga ccatctggac ctggatatca aggccctagt    1680
ggtcctggag catatggccc atctccttct gcttccgcat ccgttgcagc ctctcgttta    1740
tcttcgcctc agcctcgtc  tagagtgtct tccgctgtat cgtctttagt gtctagcgga    1800
cctacgaatg gtgctgctgt ttctggagct ttgaatagtt tagtatctca gattagtgca    1860
agtaatccag gttatcggg  atgtgatgct cttgtgcagg cattattgga attagtgtct    1920
gctcttgtgg caattctttc atctgcaagt attggccaag tcaacgtcag ctctgttagt    1980
cagtcaactc aaatgattag ccaagctctt tca                                 2013

<210> SEQ ID NO 14
<211> LENGTH: 420
<212> TYPE: DNA
<213> ORGANISM: Artificial Sequence
<220> FEATURE:
<223> OTHER INFORMATION: Artificially synthesized NR3 (ADF-3)

<400> SEQUENCE: 14
atggctagca tgactggtgg acagcaaatg ggtcgcggat ccatgggtgc ggcttctgca      60
gctgtatctg ttggaggata tggaccacaa agctcctcgg ctcctgttgc atcagcagcc    120
gcttctcgcc tttcttctcc agcggccagt tctcgtgttt catcggctgt atcatctttg    180
gtatctagtg gacctactaa tcaagctgca cttttctaata ctatcagtag cgttgtatcg    240
caagttagtg caagtaatcc tggtctttct ggttgcgatg tacttgtgca agcattgctc    300
gaagttgtat cggccctggt atctatcctt ggatcttcta gtatcgggca aattaactat    360
ggtgcctctg ctcagtacac ccaaatggta ggtcaatctg tagctcaagc ccttgctggc    420

<210> SEQ ID NO 15
<211> LENGTH: 375
<212> TYPE: DNA
<213> ORGANISM: Artificial Sequence
<220> FEATURE:
<223> OTHER INFORMATION: Artificially synthesized NR4 (ADF-4)

<400> SEQUENCE: 15
atggctagca tgactggtgg acagcaaatg ggtcgcggat ccatgggagc atatggccca      60
tctccttctg cttccgcatc cgttgcagcc tctcgtttat cttcgcctgc agcctcgtct    120
cgtgtgtctt ccgctgtatc gtctttagtg tctagcggac ctacgaatgg tgctgctgtt    180
tctggagctt tgaatagttt agtatctcag attagtgcaa gtaatccagg tttatcggga    240
tgtgatgctc ttgtgcaggc attattggaa ttagtgtctg ctcttgtggc aattctttca    300
```

```
tctgcaagta ttggccaagt caacgtcagc tctgttagtc agtcaactca aatgattagc      360
caagctcttt caggc                                                       375

<210> SEQ ID NO 16
<211> LENGTH: 2828
<212> TYPE: DNA
<213> ORGANISM: Nephila clavipes

<400> SEQUENCE: 16
gcttgcttta cctcggcagt gatatttctt ttcttagcgc agtgtgcgtc gacgtacgga       60 aggggggatta tagccaactc cccttttctca aaccctaaca cagcggaagc ttttgcacga    120
tctttcgtga gcaatattgt ttctagtgga gaatttggag cccaaggagc cgaagacttc     180
gatgacataa ttcagagtct catacaggcc cagagcatgg gcaaagggcg gcatgatacg     240
aaggccaagg cgaaagcgat gcaggtagcc cttgcttctt ctatagccga attggttatt     300
gcagaaagca gcggaggcga tgtgcaacgc aaaaccaacg ttatctccaa cgctttgaga     360
aacgccttga tgtctacaac aggcagccca acgaagagt tcgtccatga agttcaagac      420
ctcatccaga tgttatctca agaacagatc aacgaggtag atacttcagg accagggcag     480
tactacaggt cgtcttcttc cggtggagga ggtggaggac aaggaggtcc tgtagttact     540
gaaacactga ccgttacagt tggcggatcc ggtgagggc aaccttcagg tgcaggtcct      600
agtggtacag gtggatatgc accaactgga tacgccccaa gcggctcagg tgcaggtggc     660
gttcgaccta gtgcctccgg tccaagtggt agtggaccta gtggtggatc tcgtcctagt     720
agtagtggac ctagtggaac tcgtcccagc cctaatggtg caagtggatc tagccctggt     780
ggtatcgcac ctggtggatc caattctggt ggtgctggaa tatccggcgc aactggagga     840
cctgcatcca gcggctccta cggaccagga agtacaggtg aacatatgg acctagtgga      900 ggaagtgaac ctttcggacc aggagtggct ggaggaccat acagcccagg tggagctgga     960
cctggtggtg caggtggagc ctatggacca ggaggtgtag aactggtgg agccggacca    1020 ggaggttacg gacctggtgg agccggacca ggaggttatg gacctggtgg agccggacca    1080
ggaggttacg gacctggtgg agctggacca ggaggttacg gacctggtgg agctgggcct    1140
ggaggttacg gacctggtgg agctggacct ggaggttacg gacctggtgg agctggacct    1200
ggaggttacg gacctggtgg aactggacct ggtggatacg gacctggtgg aactggacct    1260
ggaggagttg gacctggagg agctggacca ggaggatatg gacctggtgg tgctggacct    1320
ggtggtgctg gacctggtgg tgctggacct ggtggtgctg gacctggtgg tgctggacct    1380
ggtggtgctg gacctggtgg atacggccct ggtggatctg gacctggtgg tgctggacct    1440
agtggtgccg gacttggtgg tgctggacct ggaggtgcgg gacttggtgg agcaggacct    1500
ggaggagcag gaaccagtgg tgccggaccc ggtggagcag gacccggtgg agcaggacaa    1560
ggtgatgctg gacccggtgg tgcaggacgt ggaggagcag gtcgtggtgg tgtaggtcgt    1620
ggtggtgcag gtcgtggagg tgcaggacgt ggtggagcta gaggtgctgg tggagcagga    1680
ggtgctggtg gagcaggagg atccggcggc acaacaatcg tagaggactt ggatattaca    1740
attgatggtg cagatggccc gataacaata tcagaagaat taacaatcgg tggagcaggc    1800
gctggaggtt ccggacccgg tggtgctgga ccaggaaacg ttggacctgg tcgctctgga    1860
ccaggaggag taggacctgg tggctctgga ccaggaggcg taggacctgg tagctttgga    1920
ccaggaggcg taggacctgg tggctccgga ccaggaggcg taggatctgg tggctccgga    1980
caaggaggag taagacctag tggctccgga ccaggtggcg taggaactgg aggcgtagga    2040
```

```
cccggtggtg ctggaggacc ttacggtcct ggtggttccg gacccggagg tgcaggaagc    2100
gctggaggaa cttatggacc tggtggtttc ggaggacccg gtggtttcgg aggacccggt    2160
ggtgctggtg gacccztacgg tccaggtggt gctggtggac cctacggacc aggtggtgct   2220 ggtggacccz acggaccagg tggtgctggt ggaccctacg gccgggtgg tgctggtgga     2280 ccctacgggc cggaggtgc tggtggatcc tacgggctgg gtggtgctgg tggatcagga     2340
ggtgtaggac ctggtggaag tggacctgga ggttatggac ccggtggagc gggacctgga    2400
ggttacggac ccggtggttc tggtccaggt ggatacggac ctggcggttc tggatctggt    2460
ggatacggac ctggaggttc tggacctggt ggttctggac ctggtggata cggacctggt    2520
ggtactggac ctggtggttc tgaatctggt ggatacggac ctggtggatc tggacctggc    2580
ggttctggac ctggtggatc tggacctggc ggttctggac ctggtggata cggacctggt    2640
ggttctggac ctagcagttt tgtacctggc ggttctggac ctggtggctc tggacccggt    2700
ggcgctggac ccggtggcgc tggacccggt ggtgttggac ttggaggtgc tggacgtggt    2760
ggagctggac gtggtggagc tggaagtgtt ggagctggac gtggtggagc tggacgtggt    2820
ggaactgg                                                             2828

<210> SEQ ID NO 17
<211> LENGTH: 2724
<212> TYPE: DNA
<213> ORGANISM: Nephila clavipes

<400> SEQUENCE: 17
ggaccaggag gtgtaggacc tggtggaagt ggacctggag gttatggacc cggtggagct      60
ggacctggag gttacggacc tggtggttct ggtccaggtg gatacggacc cggtggttcg     120
ggaccaggag gatacggacc tggcggttct ggacctggtg gatacggacc aggcggttct     180
ggacctggtg gatacggacc aggcggttct ggacctggtg gatacggacc tggtggatat     240
ggacctggtg gttctggacc tggtggatat ggacctggtg gtactggacc tggtggttct     300
ggacccggcg gatacggacc tggtggttct ggacctggcg gttctggacc tggtggatac     360
ggacctggtg gttctggacc tggcggtttt ggacctggcg gttctggacc tggtggatac     420
ggacctggtg gctctggacc cggtggtgct ggtcccggtg gtgttggacc cggtggtttt     480
ggacctggtg gtgctggacc cggtggagct ggacctggtg gtgctggacc tggtggtgct     540
ggacctggtg gtgctggacc tggtggagct ggacctggtg gtgctggacc tggtggagct     600
ggacctggtg gtgctggacc tggtggagct ggacctggtg gtgctggtgg cgctggagga     660
gcaggcggag caggaggttc aggtggagca ggaggatccg gcggtacaac aatcatagaa     720
gacttggata ttacaattga tggcgctgat ggcccgataa cgatttcaga agaattaaca     780
attagtggtg ctggaggttc cggacccggt ggtgctggac caggaggtgt agggcctggt     840
ggctccggac caggaggtgt aggacctgga ggctctggac aggaggtgt aggacctggt     900 ggttctggtc aggaggcgt aggacctggt ggtgctggtg gaccttacgg acctggcggt     960
tctggacctg gaggtgcagg cggagctgga ggacctggtg gagcatacgg acctggtgga    1020
tcatatggac ctggtggttc cggaggaccc gtggtgctg gcggaccata cggacctgga    1080
ggtgaaggac ccgtggtgc tggcggaccc tacggacctg gtggtgcagg tggaccttac    1140
ggcccaggtg gtgcaggtgg accctacgga ccaggtggtg aaggtggacc ctacggacca    1200
ggtggatcat acggaccggg tggtgctggt ggaccatacg gaccaggtgg accctacgga    1260
cctggaggtg aaggaccagg tggtgctggc ggaccctatg gaccaggagg tgtaggacct    1320
```

```
ggtggaagtg gacctggagg ttatggacct ggtggaagtg gacctggagg ttatggacct   1380
ggtggagctg gacctggagg ttacggacct ggtggttctg gtccaggtgg atacggaccc   1440
ggtggttctg gtccaggtgg atacggaccc ggtggttccg gaccaggagg atacggacct   1500
ggcggttctg gacctggtgg atacggatct ggcggtgctg gacctggtgg atacggacct   1560
ggcggttctg gacctggtgg atacggtcct ggaggttctg gacctggtgg ttatggacct   1620
ggtggtactg gacctggtgg tactggacct ggtggttctg gacctggcgg atacggacct   1680
ggtggttctg gacctggcgg ttctggacct ggcggttctg gacctggtgg atacggacct   1740
agtggttcgg gacctggtgg atacggacct agtggttctg gacctggcgg atacggtcct   1800
ggcggttctg gacctggtgg atacggaccg gtggctctg gagccggtgg tactggacct   1860
ggtggcgctg gaggagcagg cggagcagga ggttcaggtg gagcaggagg ttcaggtggt   1920
gcaggaggtt caggtggagc aggaggttca ggtggagtag gaggatccgg cggtacaaca   1980
atcaccgaag acttggatat tacaattgat ggcgcagatg cccgataac gatttcagaa    2040 gaattaacaa ttagtggtgc tggaggttct ggacccggtg gtgctggacc aggtggtgta   2100
gggcctggtg gctctggacc aggaggtgta ggacctggag tctctggacc aggaggcgta   2160
ggacctggtg gttctggacc aggaggcgta ggttctggtg gttctggacc aggaggcgta   2220
ggacctggtg gttacggacc tggaggttct ggatcaggag gcgtaggacc tggtggttac   2280
ggacctggag gttcaggagg attttacgga cctggaggtt cagaaggacc ttatggacct   2340
agtggaactt atggttctgg aggaggatat ggtcctggtg gtgctggagg accatatgga   2400
cctggaagtc ctggaggagc ttatggacct ggaagccctg gaggagctta ttatcctagc   2460
tcgcgtgttc ccgatatggt gaatggtata atgagtgcta tgcaaggatc tggttttaac   2520
taccaaatgt ttggtaatat gctatcacaa tattcgtctg gttcaggaac atgcaatcca   2580
aataatgtta atgttttgat ggatgctttg ttagctgctt tgcactgtct aagtaaccac   2640
ggatcatcat cttttgcacc ttctccaact ccggctgcta tgagtgcgta ttctaattct   2700
gtaggaagaa tgttcgctta ttaa                                          2724

<210> SEQ ID NO 18
<211> LENGTH: 52
<212> TYPE: DNA
<213> ORGANISM: Artificial Sequence
<220> FEATURE:
<223> OTHER INFORMATION: Artificially synthesized oligonucleotide

<400> SEQUENCE: 18
gatcgaggag gatccatggg acgaattcac ggctaatgaa agcttactgc ac             52

<210> SEQ ID NO 19
<211> LENGTH: 52
<212> TYPE: DNA
<213> ORGANISM: Artificial Sequence
<220> FEATURE:
<223> OTHER INFORMATION: Artificially synthesized oligonucleotide

<400> SEQUENCE: 19
agctgtgcag taagctttca ttagccgtga attcgtccca tggatcctcc tc             52

<210> SEQ ID NO 20
<211> LENGTH: 72
<212> TYPE: DNA
<213> ORGANISM: Artificial Sequence
<220> FEATURE:
<223> OTHER INFORMATION: Artificially synthesized oligonucleotide
```

```
<400> SEQUENCE: 20
tccgtacggc ccaggtgcta gcgccgcagc ggcagcggct ggtggctacg gtccgggctc    60
tggccagcag gg                                                        72

<210> SEQ ID NO 21
<211> LENGTH: 72
<212> TYPE: DNA
<213> ORGANISM: Artificial Sequence
<220> FEATURE:
<223> OTHER INFORMATION: Artificially synthesized oligonucleotide

<400> SEQUENCE: 21
ctgctggcca gagcccggac cgtagccacc agccgctgcc gctgcggcgc tagcacctgg    60
gccgtacgga cc                                                        72

<210> SEQ ID NO 22
<211> LENGTH: 60
<212> TYPE: DNA
<213> ORGANISM: Artificial Sequence
<220> FEATURE:
<223> OTHER INFORMATION: Artificially synthesized oligonucleotide

<400> SEQUENCE: 22
tccgggccag cagggcccgg gtcaacaggg tcctggccag caaggtccgg gccagcaggg    60

<210> SEQ ID NO 23
<211> LENGTH: 60
<212> TYPE: DNA
<213> ORGANISM: Artificial Sequence
<220> FEATURE:
<223> OTHER INFORMATION: Artificially synthesized oligonucleotide

<400> SEQUENCE: 23
ctgctggccc ggaccttgct ggccaggacc ctgttgaccc gggccctgct ggcccggacc    60

<210> SEQ ID NO 24
<211> LENGTH: 105
<212> TYPE: DNA
<213> ORGANISM: Artificial Sequence
<220> FEATURE:
<223> OTHER INFORMATION: Artificially synthesized oligonucleotide

<400> SEQUENCE: 24
ttctagcgcg gctgcagccg cggcagctgc gtccggcccg ggtggctacg gtccggaaaa    60
ccagggtcca tctggcccgg gtggctacgg tcctggcggt ccggg                   105

<210> SEQ ID NO 25
<211> LENGTH: 105
<212> TYPE: DNA
<213> ORGANISM: Artificial Sequence
<220> FEATURE:
<223> OTHER INFORMATION: Artificially synthesized oligonucleotide

<400> SEQUENCE: 25
cggaccgcca ggaccgtagc cacccgggcc agatggaccc tggttttccg gaccgtagcc    60
acccgggccg gacgcagctg ccgcggctgc agccgcgcta gaacc                   105

<210> SEQ ID NO 26
<211> LENGTH: 36
<212> TYPE: DNA
<213> ORGANISM: Artificial Sequence
<220> FEATURE:
<223> OTHER INFORMATION: Artificially synthesized oligonucleotide
```

<400> SEQUENCE: 26
gaaaaaccat gggtgcggct tctgcagctg tatctg            36

<210> SEQ ID NO 27
<211> LENGTH: 45
<212> TYPE: DNA
<213> ORGANISM: Artificial Sequence
<220> FEATURE:
<223> OTHER INFORMATION: Artificially synthesized oligonucleotide

<400> SEQUENCE: 27 gaaagaagc tttcattagc cagcaagggc ttgagctaca gattg    45

<210> SEQ ID NO 28
<211> LENGTH: 34
<212> TYPE: DNA
<213> ORGANISM: Artificial Sequence
<220> FEATURE:
<223> OTHER INFORMATION: Artificially synthesized oligonucleotide

<400> SEQUENCE: 28
gaaaaaccat gggagcatat ggcccatctc cttc              34

<210> SEQ ID NO 29
<211> LENGTH: 45
<212> TYPE: DNA
<213> ORGANISM: Artificial Sequence
<220> FEATURE:
<223> OTHER INFORMATION: Artificially synthesized oligonucleotide

<400> SEQUENCE: 29 gaaagaagc tttcattagc ctgaaagagc ttggctaatc atttg   45

<210> SEQ ID NO 30
<211> LENGTH: 12
<212> TYPE: PRT
<213> ORGANISM: Artificial Sequence
<220> FEATURE:
<223> OTHER INFORMATION: Artificially synthesized T7 tag

<400> SEQUENCE: 30

Met Ala Ser Met Thr Gly Gly Gln Gln Met Gly Arg
1               5                   10

<210> SEQ ID NO 31
<211> LENGTH: 216
<212> TYPE: PRT
<213> ORGANISM: Artificial Sequence
<220> FEATURE:
<223> OTHER INFORMATION: Artificially synthesized FlagN-NR

<400> SEQUENCE: 31

Gly Glu Ser Ser Gly Gly Asp Val Gln Arg Lys Thr Asn Val Ile Ser
1               5                   10                  15

Asn Ala Leu Arg Asn Ala Leu Met Ser Thr Thr Gly Ser Pro Asn Glu
            20                  25                  30

Glu Phe Val His Glu Val Gln Asp Leu Ile Gln Met Leu Ser Gln Glu
        35                  40                  45

Gln Ile Asn Glu Val Asp Thr Ser Gly Pro Gly Gln Tyr Tyr Arg Ser
    50                  55                  60

Ser Ser Ser Gly Gly Gly Gly Gly Gln Gly Gly Pro Val Val Thr
65                  70                  75                  80

Glu Thr Leu Thr Val Thr Val Gly Gly Ser Gly Gly Gly Gln Pro Ser

```
                        85                  90                  95
Gly Ala Gly Pro Ser Gly Thr Gly Gly Tyr Ala Pro Thr Gly Tyr Ala
                100                 105                 110

Pro Ser Gly Ser Gly Ala Gly Gly Val Arg Pro Ser Ala Ser Gly Pro
            115                 120                 125

Ser Gly Ser Gly Pro Ser Gly Ser Arg Pro Ser Ser Ser Gly Pro
130                 135                 140

Ser Gly Thr Arg Pro Ser Pro Asn Gly Ala Ser Gly Ser Ser Pro Gly
145                 150                 155                 160

Gly Ile Ala Pro Gly Gly Ser Asn Ser Gly Gly Ala Gly Val Ser Gly
                165                 170                 175

Ala Thr Gly Gly Pro Ala Ser Ser Gly Ser Tyr Gly Pro Gly Ser Thr
            180                 185                 190

Gly Gly Thr Tyr Gly Pro Ser Gly Gly Ser Glu Pro Phe Gly Pro Gly
        195                 200                 205

Val Ala Gly Gly Pro Tyr Ser Pro
    210                 215

<210> SEQ ID NO 32
<211> LENGTH: 648
<212> TYPE: DNA
<213> ORGANISM: Artificial Sequence
<220> FEATURE:
<223> OTHER INFORMATION: Artificially synthesized FlagN-NR

<400> SEQUENCE: 32
ggcgaaagca gcggaggcga tgtgcaacgc aaaaccaacg ttatctccaa cgctttgaga    60
aacgccttga tgtctacaac aggcagccca acgaagagt tcgtccatga agttcaagac   120
ctcatccaga tgttatctca agaacagatc aacgaggtag atacttcagg accagggcag   180
tactacaggt cgtcttcttc cggtggagga ggtggaggac aaggaggtcc tgtagttact   240
gaaacactga ccgttacagt tggcggatcc ggtgagggc aaccttcagg tgcaggtcct   300
agtggtacag gtggatatgc accaactgga tacgccccaa gcggctcagg tgcaggtggc   360
gttcgaccta gtgcctccgg tccaagtggt agtggaccta gtggtggatc tcgtcctagt   420
agtagtggac ctagtggaac tcgtcccagc cctaatggtg caagtggatc tagccctggt   480
ggtatcgcac ctggtggatc caattctggt ggtgctggag tatccggcgc aactggagga   540
cctgcatcca gcggctccta cggaccagga agtacaggtg gaacatatgg acctagtgga   600
ggaagtgaac ctttcggacc aggagtggct ggaggaccat acagccca                648

<210> SEQ ID NO 33
<211> LENGTH: 93
<212> TYPE: PRT
<213> ORGANISM: Artificial Sequence
<220> FEATURE:
<223> OTHER INFORMATION: Artificially synthesized FlagC-NR

<400> SEQUENCE: 33

Gly Ala Tyr Tyr Pro Ser Ser Arg Val Pro Asp Met Val Asn Gly Ile
1               5                   10                  15

Met Ser Ala Met Gln Gly Ser Gly Phe Asn Tyr Gln Met Phe Gly Asn
            20                  25                  30

Met Leu Ser Gln Tyr Ser Ser Gly Ser Gly Thr Cys Asn Pro Asn Asn
        35                  40                  45

Val Asn Val Leu Met Asp Ala Leu Leu Ala Ala Leu His Cys Leu Ser
    50                  55                  60
```

```
Asn His Gly Ser Ser Ser Phe Ala Pro Ser Pro Thr Pro Ala Ala Met
 65                  70                  75                  80

Ser Ala Tyr Ser Asn Ser Val Gly Arg Met Phe Ala Tyr
                 85                  90
```

<210> SEQ ID NO 34
<211> LENGTH: 279
<212> TYPE: DNA
<213> ORGANISM: Artificial Sequence
<220> FEATURE:
<223> OTHER INFORMATION: Artificially synthesized FlagC-NR

<400> SEQUENCE: 34

```
ggtgcttatt atcctagctc gcgtgttccc gatatggtga atggtataat gagtgctatg    60
caaggatctg gttttaacta ccaaatgttt ggtaatatgc tatcacaata ttcgtctggt   120
tcaggaacat gcaatccaaa taatgttaat gttttgatgg atgctttgtt agctgctttg   180
cactgtctaa gtaaccacgg atcatcatct tttgcacctt ctccaactcc ggctgctatg   240
agtgcgtatt ctaattctgt aggaagaatg ttcgcttat                          279
```

<210> SEQ ID NO 35
<211> LENGTH: 27
<212> TYPE: PRT
<213> ORGANISM: Artificial Sequence
<220> FEATURE:
<223> OTHER INFORMATION: Artificially synthesized Module K

<400> SEQUENCE: 35

```
Gly Pro Gly Gly Ala Gly Gly Pro Tyr Gly Pro Gly Gly Ala Gly Gly
  1               5                  10                  15

Pro Tyr Gly Pro Gly Gly Ala Gly Gly Pro Tyr
             20                  25
```

<210> SEQ ID NO 36
<211> LENGTH: 81
<212> TYPE: DNA
<213> ORGANISM: Artificial Sequence
<220> FEATURE:
<223> OTHER INFORMATION: Artificially synthesized Module K

<400> SEQUENCE: 36

```
ggtccgggcg gtgctggcgg tccgtacggc cctggtggcg caggtgggcc atatggtccg    60
ggcggtgcgg gcggtccgta c                                              81
```

<210> SEQ ID NO 37
<211> LENGTH: 28
<212> TYPE: PRT
<213> ORGANISM: Artificial Sequence
<220> FEATURE:
<223> OTHER INFORMATION: Artificially synthesized Module sp

<400> SEQUENCE: 37

```
Gly Gly Thr Thr Ile Ile Glu Asp Leu Asp Ile Thr Ile Asp Gly Ala
  1               5                  10                  15

Asp Gly Pro Ile Thr Ile Ser Glu Glu Leu Thr Ile
             20                  25
```

<210> SEQ ID NO 38
<211> LENGTH: 84
<212> TYPE: DNA
<213> ORGANISM: Artificial Sequence
<220> FEATURE:
<223> OTHER INFORMATION: Artificially synthesized Module sp -continued

```
<400> SEQUENCE: 38
ggtggcacca ccatcattga agatctggac atcactattg atggtgcgga cggcccgatc      60
acgatctctg aagagctgac catc                                             84

<210> SEQ ID NO 39
<211> LENGTH: 18
<212> TYPE: PRT
<213> ORGANISM: Artificial Sequence
<220> FEATURE:
<223> OTHER INFORMATION: Artificially synthesized Module X

<400> SEQUENCE: 39

Gly Gly Ala Gly Gly Ala Gly Gly Ala Gly Gly Ser Gly Gly Ala Gly
 1               5                  10                  15

Gly Ser

<210> SEQ ID NO 40
<211> LENGTH: 54
<212> TYPE: DNA
<213> ORGANISM: Artificial Sequence
<220> FEATURE:
<223> OTHER INFORMATION: Artificially synthesized Module X

<400> SEQUENCE: 40
ggtggcgctg gtggcgccgg tggcgcaggt ggctctggcg gtgcgggcgg ttcc            54

<210> SEQ ID NO 41
<211> LENGTH: 30
<212> TYPE: PRT
<213> ORGANISM: Artificial Sequence
<220> FEATURE:
<223> OTHER INFORMATION: Artificially synthesized Module Y

<400> SEQUENCE: 41

Gly Pro Gly Gly Ala Gly Pro Gly Gly Tyr Gly Pro Gly Gly Ser Gly
 1               5                  10                  15

Pro Gly Gly Tyr Gly Pro Gly Gly Ser Gly Pro Gly Gly Tyr
            20                  25                  30

<210> SEQ ID NO 42
<211> LENGTH: 90
<212> TYPE: DNA
<213> ORGANISM: Artificial Sequence
<220> FEATURE:
<223> OTHER INFORMATION: Artificially synthesized Module Y

<400> SEQUENCE: 42
ggtccgggcg gtgcgggccc aggtggctat ggtccgggcg gttctgggcc gggtggctac      60
ggtcctggcg gttccggccc gggtggctac                                       90

<210> SEQ ID NO 43
<211> LENGTH: 32
<212> TYPE: DNA
<213> ORGANISM: Artificial Sequence
<220> FEATURE:
<223> OTHER INFORMATION: Artificially synthesized oligonucleotide

<400> SEQUENCE: 43
gaaaaaccat gggcgaaagc agcggaggcg at                                    32

<210> SEQ ID NO 44
<211> LENGTH: 36
<212> TYPE: DNA
<213> ORGANISM: Artificial Sequence
```

```
<220> FEATURE:
<223> OTHER INFORMATION: Artificially synthesized oligonucleotide

<400> SEQUENCE: 44
gaaaagaagc tttcattagc ctgggctgta tggtcc                                36

<210> SEQ ID NO 45
<211> LENGTH: 33
<212> TYPE: DNA
<213> ORGANISM: Artificial Sequence
<220> FEATURE:
<223> OTHER INFORMATION: Artificially synthesized oligonucleotide

<400> SEQUENCE: 45
gaaaaaccat gggtgcttat tatcctagct cgc                                   33

<210> SEQ ID NO 46
<211> LENGTH: 42
<212> TYPE: DNA
<213> ORGANISM: Artificial Sequence
<220> FEATURE:
<223> OTHER INFORMATION: Artificially synthesized oligonucleotide

<400> SEQUENCE: 46
gaaaagaagc tttcattagc cataagcgaa cattcttcct ac                         42

<210> SEQ ID NO 47
<211> LENGTH: 90
<212> TYPE: DNA
<213> ORGANISM: Artificial Sequence
<220> FEATURE:
<223> OTHER INFORMATION: Artificially synthesized oligonucleotide

<400> SEQUENCE: 47
tccgggcggt gcgggcccag gtggctatgg tccgggcggt tctggccgg gtggctacgg       60 tcctggcggt tccggcccgg gtggctacgg                                       90

<210> SEQ ID NO 48
<211> LENGTH: 90
<212> TYPE: DNA
<213> ORGANISM: Artificial Sequence
<220> FEATURE:
<223> OTHER INFORMATION: Artificially synthesized oligonucleotide

<400> SEQUENCE: 48
gtagccaccc gggccggaac cgccaggacc gtagccaccc ggcccagaac cgcccggacc      60
atagccacct gggcccgcac cgcccggacc                                       90

<210> SEQ ID NO 49
<211> LENGTH: 84
<212> TYPE: DNA
<213> ORGANISM: Artificial Sequence
<220> FEATURE:
<223> OTHER INFORMATION: Artificially synthesized oligonucleotide

<400> SEQUENCE: 49
tggcaccacc atcattgaag atctggacat cactattgat ggtgcggacg gcccgatcac      60
gatctctgaa gagctgacca tcgg                                             84

<210> SEQ ID NO 50
<211> LENGTH: 84
<212> TYPE: DNA
<213> ORGANISM: Artificial Sequence
<220> FEATURE:
<223> OTHER INFORMATION: Artificially synthesized oligonucleotide
```

<400> SEQUENCE: 50

| gatggtcagc tcttcagaga tcgtgatcgg gccgtccgca ccatcaatag tgatgtccag | 60 |
| atcttcaatg atggtggtgc cacc | 84 |

<210> SEQ ID NO 51
<211> LENGTH: 81
<212> TYPE: DNA
<213> ORGANISM: Artificial Sequence
<220> FEATURE:
<223> OTHER INFORMATION: Artificially synthesized oligonucleotide

<400> SEQUENCE: 51

| tccgggcggt gctggcggtc cgtacggccc tggtggcgca ggtgggccat atggtccggg | 60 |
| cggtgcgggc ggtccgtacg g | 81 |

<210> SEQ ID NO 52
<211> LENGTH: 81
<212> TYPE: DNA
<213> ORGANISM: Artificial Sequence
<220> FEATURE:
<223> OTHER INFORMATION: Artificially synthesized oligonucleotide

<400> SEQUENCE: 52

| gtacggaccg cccgcaccgc ccggaccata tgcccacct gcgccaccag ggccgtacgg | 60 |
| accgccagca ccgcccggac c | 81 |

<210> SEQ ID NO 53
<211> LENGTH: 54
<212> TYPE: DNA
<213> ORGANISM: Artificial Sequence
<220> FEATURE:
<223> OTHER INFORMATION: Artificially synthesized oligonucleotide

<400> SEQUENCE: 53

| tggcgctggt ggcgccggtg gcgcaggtgg ctctggcggt gcgggcggtt ccgg | 54 |

<210> SEQ ID NO 54
<211> LENGTH: 54
<212> TYPE: DNA
<213> ORGANISM: Artificial Sequence
<220> FEATURE:
<223> OTHER INFORMATION: Artificially synthesized oligonucleotide

<400> SEQUENCE: 54

| ggaaccgccc gcaccgccag agccacctgc gccaccggcg ccaccagcgc cacc | 54 |

<210> SEQ ID NO 55
<211> LENGTH: 3238
<212> TYPE: DNA
<213> ORGANISM: Artificial Sequence
<220> FEATURE:
<223> OTHER INFORMATION: Artificially synthesized cloning vecotr pAZL

<400> SEQUENCE: 55

| tgtcgagaag tactagagga tcataatcag ccataccaca tttgtagagg ttttacttgc | 60 |
| tttaaaaaac ctcccacacc tccccctgaa cctgaaacat aaaatgaatg caattgttgt | 120 |
| tgttaacttg tttattgcag cttataatgg ttacaaataa agcaatagca tcacaaattt | 180 |
| cacaaataaa gcatttttt cactgcattc tagttgtggt ttgtccaaac tcatcaatgt | 240 |
| atcttatcat gtctggatct gatcactgct tgagcctagg agatccgaac cagataagtg | 300 |
| aaatctagtt ccaaactatt tgtcatttt taattttcgt attagcttac gacgctacac | 360 |

-continued

```
ccagttccca tctattttgt cactcttccc taaataatcc ttaaaaactc catttccacc    420
cctcccagtt cccaactatt ttgtccgccc acagcggggc attttcttc ctgttatgtt     480 tttaatcaaa catcctgcca actccatgtg acaaaccgtc atcttcggct acttttctc     540 tgtcacagaa tgaaaatttt tctgtcatct cttcgttatt aatgtttgta attgactgaa    600
tatcaacgct tatttgcagc ctgaatggcg aatgggacgc ccctgtagc ggcgcattaa     660 gcgcggcggg tgtggtggtt acgcgcagcg tgaccgctac acttgccagc gccctagcgc    720
ccgctccttt cgcttcttc ccttcctttc tcgccacgtt cgccggcttt ccccgtcaag     780
ctctaaatcg ggggctccct ttagggttcc gatttagtgc tttacggcac ctcgacccca    840
aaaaacttga ttagggtgat ggttcacgta gtgggccatc gccctgatag acggttttc     900 gccctttgac gttggagtcc acgttcttta atagtggact cttgttccaa actgaacaa     960 cactcaaccc tatctcggtc tattcttttg atttataagg gattttgccg atttcggcct    1020
attggttaaa aaatgagctg atttaacaaa aatttaacgc gaattttaac aaaatattaa    1080
cgtttacaat ttcaggtggc acttttcggg gaaatgtgcg cggaacccct atttgtttat    1140
ttttctaaat acattcaaat atgtatccgc tcatgagaca ataaccctga taatgcttc     1200 aataatattg aaaaggaag agtatgagta ttcaacattt ccgtgtcgcc cttattccct     1260
tttttgcggc attttgcctt cctgtttttg ctcacccaga aacgctggtg aaagtaaaag    1320
atgctgaaga tcagttgggt gcacgagtgg gttacatcga actggatctc aacagcggta    1380
agatccttga gagttttcgc cccgaagaac gttttccaat gatgagcact tttaaagttc    1440
tgctatgtgg cgcggtatta tcccgtattg acgccgggca agagcaactc ggtcgccgca    1500
tacactattc tcagaatgac ttggttgagt actcaccagt cacagaaaag catcttacgg    1560
atggcatgac agtaagagaa ttatgcagtg ctgccataac catgagtgat aacactgcgg    1620
ccaacttact tctgacaacg atcggaggac cgaaggagct aaccgctttt ttgcacaaca    1680
tgggggatca tgtaactcgc cttgatcgtt gggaaccgga gctgaatgaa gccataccaa    1740
acgacgagcg tgacaccacg atgcctgtag caatggcaac aacgttgcgc aaactattaa    1800
ctggcgaact acttactcta gcttcccggc aacaattaat agactggatg gaggcggata    1860
aagttgcagg accacttctg cgctcggccc ttccggctgg ctggtttatt gctgataaat    1920
ctggagccgg tgagcgtggg tctcgcggta tcattgcagc actggggcca gatggtaagc    1980
cctcccgtat cgtagttatc tacacgacgg ggagtcaggc aactatggat gaacgaaata    2040
gacagatcgc tgagataggt gcctcactga ttaagcattg gtaactgtca gaccaagttt    2100
actcatatat actttagatt gatttaaaac ttcattttta atttaaaagg atctaggtga    2160
agatcctttt tgataatctc atgaccaaaa tcccttaacg tgagttttcg ttccactgag    2220
cgtcagaccc cgtagaaaag atcaaaggat cttcttgaga tcctttttt ctgcgcgtaa     2280 tctgctgctt gcaaacaaaa aaccaccgc taccagcggt ggtttgtttg ccggatcaag     2340
agctaccaac tcttttccg aaggtaactg gcttcagcag agcgcagata ccaaatactg     2400
tccttctagt gtagccgtag ttaggccacc acttcaagaa ctctgtagca ccgcctacat    2460
acctcgctct gctaatcctg ttaccagtgg ctgctgccag tggcgataag tcgtgtctta    2520
ccgggttgga ctcaagacga tagttaccgg ataaggcgca gcggtcgggc tgaacggggg    2580
gttcgtgcac acagcccagc ttggagcgaa cgacctacac cgaactgaga tacctacagc    2640
gtgagcatta gaaagcgcc acgcttcccg aagggagaaa ggcggacagg tatccggtaa     2700
gcggcagggt cggaacagga gagcgcacga gggagcttcc agggggaaac gcctggtatc    2760
```

```
                                                            -continued tttatagtcc tgtcgggttt cgccacctct gacttgagcg tcgatttttg tgatgctcgt      2820
caggggggcg gagcctatgg aaaaacgcca gcaacgcggc cttttttacgg ttcctggcct     2880 tttgctggcc ttttgctcac atgttctttc ctgcgttatc ccctgattct gtggataacc     2940
gtattaccgc ctttgagtga gctgataccg ctcgccgcag ccgaacgacc gagcgcagcg     3000
agtcagtgag cgaggaagcg gaagagcgcc tgatgcggta ttttctcctt acgcatctgt     3060
gcggtatttc acaccgcaga ccagccgcgt aacctggcaa aatcggttac ggttgagtaa     3120
taaatggatg ccctgcgtaa gcgggtgtgg gcggacaata aagtcttaaa ctgaacaaaa     3180
tagatcgagg aggatccatg ggacgaattc acggctaatg aaagcttact gcacagct      3238
```

METHODS OF PRODUCING NANO- AND MICROCAPSULES OF SPIDER SILK PROTEINS

The present invention is directed to a method of producing nano- and microcapsules from spider silk proteins. The invention is further directed to nano- or microcapsules obtainable by this method as well as pharmaceutical, cosmetical and food compositions containing same.

Small-scale structures are of great interest as transport vesicles and as potential building blocks for future devices. One task is to be able to encapsulate reactants or particles at small scales and to allow triggered release of the encapsulated matter after placing them at a specific location. One solution for such problem is the use of chemical vesicles, so called nano-capsules. The nano-capsules are designed to set the reactants free upon an external trigger or stimulus. Several problems arise from such quest: the most important one is how to build such nano-capsules in a defined way around e.g. chemically or biologically active reactants.

Recently, "hybrid" stimuli-responsive nano-capsules have been developed to fulfill such needs. The structures (vesicles but also micelles) are obtained from the self-assembly of e.g. amphiphile polybutadiene (PB)-b-poly(glutamic acid) (PGA) diblock copolymers, which have a pH-sensitive conformation. The pH-sensitivity can be used to unload the vesicles. Those PB-b-PGA copolymers bearing a cross-linkable hydrophobic block and a hydrophilic peptidic block have been synthesized by combining anionic and ring-opening polymerization (Chécot et al., 2002). The polydispersity of the copolymers is small enough to obtain well defined self-assembled aggregates. For example a PB40-b-PGA100 copolymer when in water forms closed bilayer vesicles called polymersomes (Won et al., 1999). One property of the vesicles is that they respond to an external pH shift by changing in size (FIG. 1). This transition upon pH changes is reversible and only moderately sensitive to salinity, since it is not based on a simple polyelectrolyte swelling effect, but on the peptidic nature of the PGA block (FIG. 1). These vesicles are not only able to encapsulate low molecular weight compounds (like solvent molecules such as fluorophors (Chécot et al., 2003)), but can also stabilize larger nanoparticles. The disadvantage of such systems is the partial incompatibility with biological systems, which usually are highly sensitive to dramatic pH changes, since pH changes can result in a loss in biological activity of the encapsulated sample.

FIG. 1 for illustration shows (a) Dynamic Light Scattering of the peptosome's hydrodynamic radius $R_H$ as a function of NaCl concentration and pH. (b) Schematic representation of the peptosome and its change in size as function of pH due to a coil to α-helix secondary structure transition in the peptide part.

Another established encapsulation method is the self-assembly of colloidal particles at the oil/water interphase. The driving force for the self-assembly process is the minimization of the total surface energy—thus a wide variety of particles and solvents can be used. Such stabilized emulsions are well known as Pickering emulsions. The stabilization or crosslinking of the particles leads to mechanical stable cages, which can than be transferred to the continuous phase. The advantages of the so called colloidosomes are the control of the encapsulate and the ease of tuning the mechanical and chemical stability of the outer shell. The self-assembly of the particles results in an almost crystalline structure and thus holes between the particles will occur. These holes are a size selective filter which allows the control of the diffusion across the membrane (Dinsmore et al., 2000). The whole process can be performed in a biocompatible way. However, the colloidal particles themselves are not necessarily biocompatible.

WO 02/47665 describes a method for making self-assembled, selectively permeable elastic microscopic structures, referred to as colloidosomes, that have controlled pore-size, porosity and advantageous mechanical properties. The method comprises: (a) providing particles formed from a biocompatible material in a first solvent; (b) forming an emulsion by adding a first fluid to said first solvent, said emulsion being defined by droplets of said first fluid surrounded by said first solvent; (c) coating the surface of said droplets with said particles; and (d) stabilizing said particles on said surface of said droplet to form colloidosomes having a yield strength of at least about 20 Pascals. WO 02/47665 uses biocompatible synthetic polymers for producing these colloidosomes. Examples are polystyrene, polymethylmethacrylate, polyalkylenes, silica and combinations thereof. The particles from which the colloidosomes are to be obtained are stabilized for example by sintering, chemical crosslinking and the like. However, the method of preparing those colloidosomes is comparably difficult and the colloidal particles used may show harmful properties for in vivo applications due to their artificial and non natural nature. By using colloidal particles limits also the size range of the shells, since using colloids limits the minimal size bag with defined holes.

Therefore, it is a problem underlying the present invention to provide nano- and microcapsules, which are highly biocompatible and thus suitable for in vivo applications. It is another problem of this invention to obtain nano- and microcapsules, which are capable to accommodate different types and varying amounts of effective agents or nutritions etc. A further problem underlying the present invention is to provide nano- and microcapsules which are biodegradable, i.e. which are capable of a controlled release of said effective agents etc. in vivo, for example in topical or systemic applications.

These problems are solved by the subject-matter of the independent claims. Preferred embodiments are set forth in the dependent claims.

In the present invention, it surprisingly turned out that spider silk proteins may serve as a base for forming micro- and nanocapsules which can be used for various in vivo applications. It in particular turned out that this can be done by an improved method of producing said capsules, which does circumvent the need of using steps to link or stabilize the particles from which the capsules are formed by addition of chemicals like crosslinkers or which requires sintering or the like which could have deleterious effects on the agents to be packaged into said micro- and nanocapsules.

Since most currently used encapsulation techniques (see for example WO 02/47665) rely on non-biological particles or macromolecules, the inventors developed a new stable encapsulation process based on self-assembling spider silk proteins. Unlike other encapsulation technologies, in the present method the hydrophobic/hydrophilic nature of the emulsion surface is not only used to assemble colloid particles, but it is also used as the driving force for the colloid immobilization through coalescence and polymer network formation (stabilization). This process represents not only a method to produce polymeric nano- and microcapsules formed from a new class of biocompatible colloids, it also represents a novel approach to polymer network formation using proteins. The big advantage of nano- and microcapsules formed from this method is the biocompatibility and the functionality of the microcapsules imparted by the proteins. This enables the control of the release mechanisms by several means: pH changes, temperature changes, or activity of proteases.

For example, the nano- or microcapsules might be destroyed and their ingredients might be released in vivo chemically, physically (for example by shear forces) or biologically (by proteolytic digestion).

The self-assembly of the spider silk proteins at the interface was achieved by introducing the protein into the water phase of a water/oil emulsion (see FIG. 2). The minimization of surface energy was driving the proteins to the interface and induced an aggregation of the monomers to a dense polymer network (FIG. 3).

The spider bags/balloons formed from this process are for example filled with the contents of the water phase and can exist in organic solvents, alcohols as well as in water (FIG. 3). Therefore, they are showing an unexpected stability in strongly differing environments. In principal the self-assembly of proteins at an inverse emulsion surface is also possible—thus encapsulating the content of the oil phase (see also below).

Strikingly, the bags/balloons can be filled with proteins, chemical reactants, nano- and micrometer scaled particles, etc., which is exemplarily shown by filling the particles with fluorescently (FITC)-labeled Dextran particles (FIG. 4).

The impermeability of the membrane and the mechanical stability of the bags against osmotic stresses are both relatively high, considering the thickness of the membrane. Electron microscopy images reveal that the thickness is between 10 and 70 nm (FIG. 5).

In the present approach synthetic spider silk proteins have been employed, in particular the synthetic sequence of $C_{16}$ (Huemmerich et al., 2004) to create a biological encapsulation of active agents.

Spider silks in general are protein polymers that display extraordinary physical properties, but there is only limited information on the composition of the various silks produced by different spiders (see Scheibel, 2004). Among the different types of spider silks, draglines from the golden orb weaver *Nephila clavipes* and the garden cross spider *Araneus diadematus* are most intensely studied. Dragline silks are generally composed of two major proteins and it remains unclear whether additional proteins play a significant role in silk assembly and the final silk structure. The two major protein components of draglines from *Araneus diadematus* are ADF-3 and ADF-4 (Araneus Diadematus Fibroin).

Genes coding for spider silk-like proteins were generated using a cloning strategy, which was based on a combination of synthetic DNA modules and PCR-amplified authentic gene sequences (Huemmerich et al., 2004). The dragline silk proteins ADF-3 and ADF-4 from the garden spider *Araneus diadematus* were chosen as templates for the synthetic constructs. A seamless cloning strategy allowed controlled combination of different synthetic DNA modules as well as authentic gene fragments. A cloning vector was designed comprising a cloning cassette with a spacer acting as placeholder for synthetic genes (Huemmerich et al., 2004).

To mimic the repetitive sequence of ADF-4 a single conserved repeat unit has been designed to gain one consensus module termed C, which was multimerized to obtain the repetitive protein $C_{16}$, which was employed in the given approach as an example.

There are many possible applications for the presented spider silk bags/balloons, ranging from functional food to pharmaceutical to cosmetical applications. For example the encapsulation in food technology could protect certain ingredients such as vitamins from an oxidizing environment. In another food technology application, ingredients such as fish oil could be hidden from taste. In pharmaceutical applications the diffusion barrier of the protein shell allows for slow (controlled) release processes for the encapsulated material. The further design of the protein shells could result in a defined release container, which liberates the content only after activation using certain proteases or other triggers. In cosmetics the transport of water active ingredients into the skin could be facilitated by the presented bags/balloons, after slow degradation of the protein shell, e.g. by proteases of the skin. Further, mechanical shearing can be used to liberate the content upon exposure to the skin.

The present invention in particular is directed to the following aspects and embodiments:

According to a first aspect, the present invention is directed to a method of producing nano- and microcapsules comprising the steps of:
a) providing spider silk proteins;
b) forming a solution or suspension of said proteins in a suitable solvent;
c) generating an emulsion of at least two phases, said emulsion containing the solution or suspension formed in b) as a first phase and at least one further phase, which is substantially immiscible with said first phase;
d) forming a polymer network of the spider silk proteins at the interface of the at least two phases;
e) separating the protein polymer network generated in (d) from the emulsion.

As explained above, it unexpectedly turned out that forming the polymer network in step d) does not require the addition of any further ingredients (for example crosslinkers) and there is no need for additional steps as sintering, crosslinking etc.

It is noted that the term "spider silk protein" as used herein does not only comprise all natural sequences but also all artificial or synthetic sequences which were derived therefrom.

Accordingly, the spider silk sequences may be derived from sequences which are termed "authentic" herein. This term means that the underlying nucleic acid sequences are isolated from their natural environment without performing substantial amendments in the sequence itself. The only modification, which is accepted to occur, is where the authentic nucleic acid sequence is modified in order to adapt said sequence to the expression in a host without changing the encoded amino acid sequence. Preferred sequences are NR3 (SEQ ID NO: 10; derived from ADF-3) and NR4 (SEQ ID NO: 11; derived from ADF-4). In both sequences, for more efficient translation, the codon AGA (Arg), which is rarely translated in *E. coli*, was mutated to CGT (Arg) using PCR mutagenesis.

The authentic non-repetitive sequences are preferably derived from the amino terminal non-repetitive region (flagelliform proteins) and/or the carboxy terminal non-repetitive region (flagelliform and dragline proteins) of a naturally occurring spider silk protein. Preferred examples of those proteins will be indicated below.

According to a further embodiment, the authentic non-repetitive sequences are derived from the amino terminal non-repetitive region (flagelliform proteins) and/or the carboxy terminal non-repetitive region (flagelliform and dragline proteins) of a naturally occurring spider silk protein.

Preferred authentic sequences of flagelliform proteins are the amino acid sequence and nucleic acid sequence of FlagN-NR (SEQ ID NOs: 31 and 32) and FlagC-NR (SEQ ID NOs: 33 and 34).

The recombinant spider silk proteins of the invention generally may be derived from spider dragline proteins from the spider's major ampullate gland and/or from proteins derived from the flagelliform gland.

According to an embodiment, the recombinant (synthetic/artificial) spider silk proteins which can be used in the present invention generally are derived from spider dragline proteins from the spider's major ampullate gland and/or from proteins derived from the flagelliform gland.

It is generally preferred to select the dragline and/or flagellifonm sequences from dragline or flagellifonm proteins of orb-web spiders (Araneidae and Araneoids).

More preferably the dragline proteins and/or flagelliform proteins are derived from one or more of the following spiders: *Arachnura higginsi, Araneus circulissparsus, Araneus diadematus, Argiope picta*, Banded Garden Spider (*Argiope trifasciata*), Batik Golden Web Spider (*Nephila antipodiana*), Beccari's Tent Spider (*Cyrtophora beccarii*), Bird-dropping Spider (*Celaenia excavata*), Black-and-White Spiny Spider (*Gasteracantha kuhlii*), Black-and-yellow Garden Spider (*Argiope aurantia*), Bolas Spider (*Ordgarius furcatus*), Bolas Spiders—Magnificent Spider (*Ordgarius magnificus*), Brown Sailor Spider (*Neoscona nautica*), Brown-Legged Spider (*Neoscona rufofemorata*), Capped Black-Headed Spider (*Zygiella calyptrata*), Common Garden Spider (*Parawixia dehaani*), Common Orb Weaver (*Neoscona oxancensis*), Crab-like Spiny Orb Weaver (*Gasteracantha cancriformis* (elipsoides)), Curved Spiny Spider (*Gasteracantha arcuata*), *Cyrtophora moluccensis, Cyrtophora pamasia, Dolophones conifera, Dolophones turrigera*, Doria's Spiny Spider (*Gasteracantha doriae*), Double-Spotted Spiny Spider (*Gasteracantha mammosa*), Double-Tailed Tent Spider (*Cyrtophora exanthematica*), *Aculeperia ceropegia, Eriophora pustulosa*, Flat Anepsion (*Anepsion depressium*), Four-spined Jewel Spider (*Gasteracantha quadrispinosa*), Garden Orb Web Spider (*Eriophora transmarina*), Giant Lichen Orbweaver (*Araneus bicentenarius*), Golden Web Spider (*Nephila maculata*), Hasselt's Spiny Spider (*Gasteracantha hasseltii*), *Tegenaria atrica, Heurodes turrita*, Island Cyclosa Spider (*Cyclosa insulania*), Jewel or Spiny Spider (*Astracantha minax*), Kidney Garden Spider (*Araneus mititficus*), Laglaise's Garden Spider (*Enrovixia laglaisei*), Long-Bellied Cyclosa Spider (*Cyclosa bifida*), Malabar Spider (*Nephilengys malabarensis*), Multi-Coloured St Andrew's Cross Spider (*Argiope versicolor*), Ornamental Tree-Trunk Spider (*Herennia ornatissima*), Oval St. Andrew's Cross Spider (*Argiope aemula*), Red Tent Spider (*Cyrtophora unicolor*), Russian Tent Spider (*Cyrtophora hirta*), Saint Andrew's Cross Spider (*Argiope keyserlingi*), Scarlet *Acusilas* (*Acusilas coccineus*), Silver *Argiope* (*Argiope argentata*), Spinybacked Orbweaver (*Gasteracantha cancrifonmis*), Spotted Orbweaver (*Neoscona domiciliorum*), St. Andrews Cross (*Argiope aetheria*), St. Andrew's Cross Spider (*Argiope Keyserlingi*), Tree-Stump Spider (*Poltys illepidus*), Triangular Spider (*Arkys clavatus*), Triangular Spider (*Arkys lancearius*), Two-spined Spider (*Poecilopachys australasia*), *Nephila* species, e.g. *Nephila clavipes, Nephila senegalensis, Nephila madagascariensis* and many more (for further spider species, see also below). Most preferred, the dragline proteins are derived from Araneus diadematus and the flagellifonm proteins are derived from *Nephila clavipes*.

In the context of this invention, it should be clear that a recombinant spider silk protein may not only comprise protein sequences from one species, but may also contain sequences derived from different spider species. As an example, the one or more synthetic repetitive spider silk protein sequences might be derived from one species, the one or more authentic non-repetitive spider silk protein sequences from another. As a further example, it is also possible to design a recombinant spider silk protein, which contains more than one type of a repetitive sequence, wherein the different types are derived from different species.

According to one preferred embodiment, the dragline protein is wild type ADF-3, ADF-4, MaSp I, MaSp II and the flagelliform protein is FLAG. The term ADF-3/-4 is used in the context of MaSp proteins produced by Araneus diadematus (Araneus diadematus fibroin-3/-4). Both proteins, ADF-3 and 4 belong to the class of MaSp II proteins (major ampullate spidroin II).

In a further embodiment, the nucleic acid sequence provided is ADF-3 (SEQ ID NO:1) and/or ADF-4 (SEQ ID NO: 2), or a variant thereof.

It is noted that two different kinds of ADF-3 and ADF-4 coding sequences and proteins are contemplated in this invention: first, the already published sequence of ADF-3 and ADF-4 (herein: "wild type" sequence) and, second, a variant thereof, encoded by SEQ ID NO: 1 (ADF-3) and 2 (ADF-4). The wild type sequences were already published and are available under the accession numbers U47855 and U47856 (SEQ ID NO: 8 and 9).

Further spider silk proteins, which can be used in this invention (i.e. alone or in combination with further proteins) and their database accession numbers are:
spidroin 2 *[Araneus bicentenarius]*gi|2911272
major ampullate gland dragline silk protein-1 *[Araneus ventricosus]*gi|27228957
major ampullate gland dragline silk protein-2 *[Araneus ventricosus]*gi|27228959 ampullate spidroin 1
[*Nephila madagascariensis]*gi|13562006
major ampullate spidroin 1*[Nephila senegalensis]* gi|13562010
major ampullate spidroin 1 *[Latrodectus geometricus]* gi|13561998
major ampullate spidroin 1 *[Argiope trifasciata]*gi|13561984
major ampullate spidroin 1 *[Argiope aurantia]*gi|13561976
dragline silk protein spidroin 2 *[Nephila clavata]* gi|16974791
major ampullate spidroin 2 *[Nephila senegalensis]* gi|13562012
major ampullate spidroin 2 *[Nephila madagascariensis]* gi|13562008
major ampullate spidroin 2 *[Latrodectus geometricus]* gi|13562002

According to another preferred embodiment, the flagelliform protein is SEQ ID NO: 6 (Flag-N) and/or SEQ ID NO: 7 (Flag-C) or a variant thereof.

However, also already known and published flagelliform sequences may be used herein, in particular the following:
Flagelliform silk protein partial cds *[Nephila clavipes]* gi|2833646
Flagelliform silk protein partial cds *[Nephila clavipes]* gi|2833648

In one preferred embodiment, the recombinant spider silk protein comprises one or more synthetic repetitive sequences containing one or more polyalanine containing consensus sequences. Those polyalanine sequences may contain from 6 to 9 alanine residues. See, for example SEQ ID NO: 1, containing several polyalanine motifs of 6 alanine residues.

Preferably, the polyalanine containing consensus sequence is derived from ADF-3 and has the amino acid sequence of SEQ ID NO: 3 (module A) or a variant thereof. Module A contains a polyalanine having 6 alanine residues. A further preferred polyalanine containing consensus sequence, derived from ADF-4, is module C (SEQ ID NO: 5), containing 8 alanine residues.

According to a further preferred embodiment, in the recombinant spider silk protein of the invention, the synthetic repetitive sequence is derived from ADF-3 and comprises one or more repeats of the amino acid sequence of SEQ ID NO: 4 (module Q) or a variant thereof.

In more general words, a synthetic repetitive sequence may also contain the general motifs: GGX or GPGXX, i.e. glycine rich regions. As mentioned above, these regions will provide flexibility to the protein and thus, to the thread formed from the recombinant spider silk protein containing said motifs.

It is noted that the specific modules for the synthetic repetitive sequence for use in the present invention can also be combined with each other, i.e. modules (repeat units) combining A and Q, Q and C etc. are also encompassed by the present invention. Although the number of the modules to be introduced in the spider silk protein is not restricted, it is preferred to employ a number of modules of the synthetic repetitive sequence for each recombinant protein which number is preferably ranging from 5-50 modules, more preferably 10-40 and most preferably between 15-35 modules.

The synthetic repetitive sequence preferably comprises one or more of (AQ) and/or (QAQ) as repeat units. Even more preferred, the synthetic repetitive sequence is $(AQ)_{12}$, $(AQ)_{24}$, $(QAQ)_8$ or $(QAQ)_{16}$.

Whenever the synthetic repetitive sequence is derived from ADF-4, it may preferably comprise one or more repeats of the amino acid sequence of SEQ ID NO: 5 (module C) or a variant thereof, as mentioned above, wherein the overall synthetic repetitive sequence is $C_6$ or $C_{32}$.

Preferred embodiments for the complete recombinant spider silk proteins of the invention are $(QAQ)_8NR3$, $(QAQ)_{16}NR3$, $(AQ)_{12}NR3$, $(AQ)_{24}NR3$, $C_{16}NR4$ and $C_{32}NR4$ i.e. proteins which comprise or consist of said sequences.

It is noted that the above configuration of the synthetic repetitive sequence (using the A, Q and C system) also applies to all other repeat units disclosed above, for example all polyalanine containing sequences can be taken for A and/or C and all glycine rich sequences may be used as Q.

New modules for synthetic repetitive sequences derived from flagelliform sequences are modules K (SEQ ID NO: 35 and 36), sp (SEQ ID NO: 37 and 38), X (SEQ ID NO: 39 and 40), and Y (SEQ ID NO: 41 and 42):

The synthetic repetitive sequence also preferably comprises or consists of $Y_8$, $Y_{16}$, $X_8$, $X_{16}$, $K_8$, $K_{16}$. Furthermore, it is also possible, to combine those sequences derived from ADF-3 and ADF-4 and Flag in one recombinant sequence.

In the present invention it is however strongly preferred to employ spider silk proteins in step a) which are selected from or containing sequences of the group of ADF-4 sequences and derivatives thereof including $C_{16}$, $C_{16}NR4$, $C_{32}$ and/or $C_{32}NR4$.

In the present invention the spider silk proteins can be further engineered to contain single amino acid substitutions or direct chemical modifications before capsule production, or the latter also after capsule production. This can be used to introduce e.g. specific binding affinities to the bags or to introduce protease specific amino acid sequences. This may result in a controlled release of the encapsulate by proteolytic digestion of the silk membrane.

By introducing e.g. single cysteines crosslinking of the bag or the covalent coupling of different functional groups can be achieved. For example, replacing nucleic acids encoding one or more amino acids in a spider silk protein by a lysine or cysteine encoding nucleic acid sequence, and/or adding a nucleic acid sequence containing nucleic acids encoding lysine and/or cysteine to said sequence, may achieve this.

Further, agents may be coupled to the spider silk proteins before and after formation of the nano- or microcapsules in order to direct the capsules to specific cells or tissues. This can be achieved, for example, by introducing or covalent coupling of specific RGD sequences. Thus, RGD peptides may be cross-linked to the spider silk proteins before and after formation of the nano- or microcapsules. Examples for cyclic RGD molecules are indicated in FIG. 10.

Furthermore, cell or tissue specific antibodies and cell or tissue specific receptors might be coupled to the spider silk proteins to direct the capsules to a specific target.

According to a further embodiment, the solvent in b) and/or the solvents of the at least one further phase is selected from the group consisting of hydrophilic solvents, preferably water, alcohols like ethanol, glycerol, or lipophilic solvents, preferably natural oils, such as oils of plant or animal origin, synthetic oils, such as miglyol, silicon oil, organic solvents, such as aromatic hydrocarbons, for example toluene, benzene etc.

It is noted that one single phase may contain also more than one solvent (i.e. a mixture) as long as the solvents are substantially identical. "Substantially identical" means that the solvents are having similar solubility properties thus forming only one common phase. Thus, "substantially identical" solvents include solvents in which one can not observe separate phases if the solvents are blended. As an example, two or more lipophilic solvents may be combined into one phase, for example a plant oil (for example olive oil and castor oil) and miglyol and/or hexadecane. Or, as an alternative, a hydrophilic phase may comprise two or more hydrophilic components, for example water, glycerol and the like.

As mentioned above, the only requirement is that the emulsion system for producing the nano- and microcapsules of the invention has at least two phases, wherein the phases are substantially immiscible.

All known emulsion types may be employed in step c) of the present method, for example W/O, O/W, O/W/O or W/O/W type emulsions. These emulsion types are well known in the art and for further information it is for example referred to "Remington's Pharmaceutical Sciences", Mack Publishing Co., Easton, Pa., latest edition or further available information.

A preferred method for forming the emulsions of the present invention is to produce a mini-emulsion. Mini-emulsions are dispersions of critically stabilized oil droplets with a size between 50 and 500 nm prepared by shearing a system containing oil, water, a surfactant and a hydrophobic agent. Polymerizations in such mini-emulsions, when carefully prepared, result in particles which have about the same size as the initial droplets. This means that the appropriate formulation of a mini-emulsion suppresses coalescence of droplets or Ostwald ripening. The preparation of the mini-emulsion is done by high shear devices such as ultrasound and high-pressure homogenizers. It is referred to the various publications of K. Landfester and coworkers.

In case of an emulsion of the W/O type, the W (hydrophilic) phase is forming the emulsion droplets and in this case, the spider silk proteins are contained in the W phase. The O phase is the lipophilic phase and forms the continuous phase.

In case of an emulsion of the O/W type, the O (lipophilic) phase is forming the emulsion droplets and in this case, the spider silk proteins are contained in the O phase. The W phase is the hydrophilic phase and forms the continuous phase.

The surfactants used in the above emulsions may be selected from those compounds, the skilled person will use based on the available knowledge in the field of pharmaceutical and related sciences. An exemplary selection of surfactants for use in obtaining the present emulsions are fatty acid esters of glycerols, sorbitol and other multifunctional alcohols, preferably, glycerol monostearate, sorbitan monolaurate, or sorbitan monoleate; poloxamines; polyoxyethylene ethers and polyoxyethylene esters; ethoxylated triglycerides; ethoxylated phenols and ethoxylated diphenols; metal salts of fatty acids, metal salts of fatty alcohol sulfates, sodium lauryl sulfate; and metal salts of sulfosuccinates: polysorbates, more preferably polysorbate 20, 40, 60 and 80: poloxamers, polyoxyethylene glycols; and mixtures of said substances.

However, it is explicitly noted that it is not an essential feature of this invention to use a surfactant. The skilled artisan is aware of emulsion systems, which do not require surfactants.

In a preferred embodiment of the present invention, the solvent used in 1b) further contains one or more pharmaceutical agents, cosmetical agents, foodstuffs or food additives. In other words, the additional ingredients usually will be present in the phase, which is also containing the spider silk proteins. In this case, the one or more ingredients/agents will be encapsulated into the polymer network which is formed at the phase-interface.

As an alternative, it is also possible to add the above mentioned agents to the continuous phase, which does not contain the spider silk proteins. In this case, the nano- and microcapsules of the invention will be coated by said agents.

As a further alternative, the agents may be introduced into the nano- and microcapsules of the invention after they have been obtained by the present method.

This can be done by swelling the membrane with certain solvents and letting the encapsulate (effective agent) diffuse inside. Swelling could also be done by temperature, pressure or not only solvents but also other chemical means (such as chemical agents, pH, and others)

It is also possible to incorporate the encapsulate into the membrane. This approach may give amended or improved release properties than encapsulating the encapsulate into it.

The type of agent which is additionally incorporated into the nano- and microcapsules of the invention is not restricted in any way.

For example, the pharmaceutical agent may be selected from the group consisting of analgesics; hypnotics and sedatives; drugs for the treatment of psychiatric disorders such as depression and schizophrenia; anti-epileptics and anticonvulsants; drugs for the treatment of Parkinson's and Huntington's disease, aging and Alzheimer's disease; drugs aimed at the treatment of CNS trauma or stroke; drugs for the treatment of addiction and drug abuse; chemotherapeutic agents for parasitic infections and diseases caused by microbes; immunosuppressive agents and anti-cancer drugs; hormones and hormone antagonists; antagonists for non-metallic toxic agents; cytostatic agents for the treatment of cancer; diagnostic substances for use in medicine; immunoactive and immunoreactive agents; antibiotics; antispasmodics; antihistamines; antinauseants; relaxants; stimulants; cerebral dilators; psychotropics; vascular dilators and constrictors; anti-hypertensives; drugs for migraine treatment; hypnotics, hyperglycemic and hypoglycemic agents; anti-asthmatics; antiviral agents; and mixtures thereof.

Foodstuffs and food additives may be selected from the group consisting of vitamines (ascorbic acid, tocopherol acetate and the like), minerals (calcium, magnesium, potassium, sodium, for example), trace elements (selenium), extracts of natural origin, natural oils (fish oil) etc.

Cosmetical agents may be selected for example from tocopherol acetate, oils of natural or synthetic origin, panthenol, plant extracts, UV absorbing agents, desinfectants, anti-irritant agents, repellants.

It is noted that the agents might be present in the solvent in dissolved, suspended or solid form. In the latter case, a solid core is provided which is coated by the spider silk proteins of the present invention.

In a preferred embodiment, the separation of the polymer network in step e) is done by means of centrifugation or by destroying the emulsion formed in step c) and forming a one-phase solution. However, also other methods may be used in order to separate the nano- and microcapsules of the present invention from the emulsion system.

The temperature used in steps b)-e) is 5-40° C., preferably 10-30 and more preferably room temperature. The pH used in steps b)-e) is 3-9, preferably 5-8, more preferably 7.

The size of the emulsion droplets and the nano- and microparticles derived therefrom is preferably from 10 nm to 40 µm, preferably between 500 nm and 10 µm, most preferably about 5 µm. The wall thickness of the obtained nano- and microcapsules preferably is between 5 and 100 nm, more preferably between 10 and 70 nm (see for example FIG. 5).

In a second aspect, the present invention provides nano- and microcapsules obtainable by the method as disclosed above.

A third aspect of the present invention is directed to a pharmaceutical composition containing nano- and microcapsules as defined above and one or more pharmaceutically acceptable carriers. Thus, the active components of the present invention are preferably used in such a pharmaceutical composition in doses mixed with an acceptable carrier or carrier material, that the disease can be treated or at least alleviated. Such a composition can (in addition to the active component and the carrier) include filling material, salts, buffer, stabilizers, solubilizers and other materials, which are known state of the art.

The term "pharmaceutically acceptable" is defined as non-toxic material, which does not interfere with effectiveness of the biological activity of the active component. The choice of the carrier is dependent on the application.

The pharmaceutical composition can contain additional components which enhance the activity of the active component or which supplement the treatment. Such additional components and/or factors can be part of the pharmaceutical composition to achieve a synergistic effects or to minimize adverse or unwanted effects.

Techniques for the formulation or preparation and application/medication of compounds of the present invention are published in "Remington's Pharmaceutical Sciences", Mack Publishing Co., Easton, Pa., latest edition (see also above). An appropriate application can include for example oral, dermal or transmucosal application and parenteral application, including intramuscular, subcutaneous, intramedular injections as well as intrathecal, direct intraventricular, intravenous, intraperitoneal or intranasal injections.

In a fourth aspect, the present invention provides a cosmetical or food product containing nano- and microcapsules as disclosed hereinabove.

All publications, patent applications, patents, and other references mentioned herein are incorporated by reference in their entirety. In case of conflict, the present specification, including definitions, will control. In addition, the materials, methods, and examples are illustrative only and not intended to be limiting.

The invention is now further illustrated by the accompanying figures, in which:

FIG. 1 shows (a) Dynamic Light Scattering of the peptosome's hydrodynamic radius $R_H$, as a function of NaCl concentration and pH. (b) Schematic representation of the peptosome and its change in size as function of pH due to a coil to α-helix secondary structure transition in the peptide part.

FIG. 2 is an schematic illustration of the spider bag/balloon formation process. (A) An aqueous protein suspension is emulsified in toluene. (B) Protein adsorbs at the water-toluene interface and denatures forming a polymer network (Inset). (C) Once adsorbed, the protein network can be transferred into water by centrifugation. The final bag/balloon structures have water on the inside and water on the outside. (D) Alternatively, once adsorbed, the protein network can be transferred into a one-phase solution through the addition of ethanol.

Figure 6:
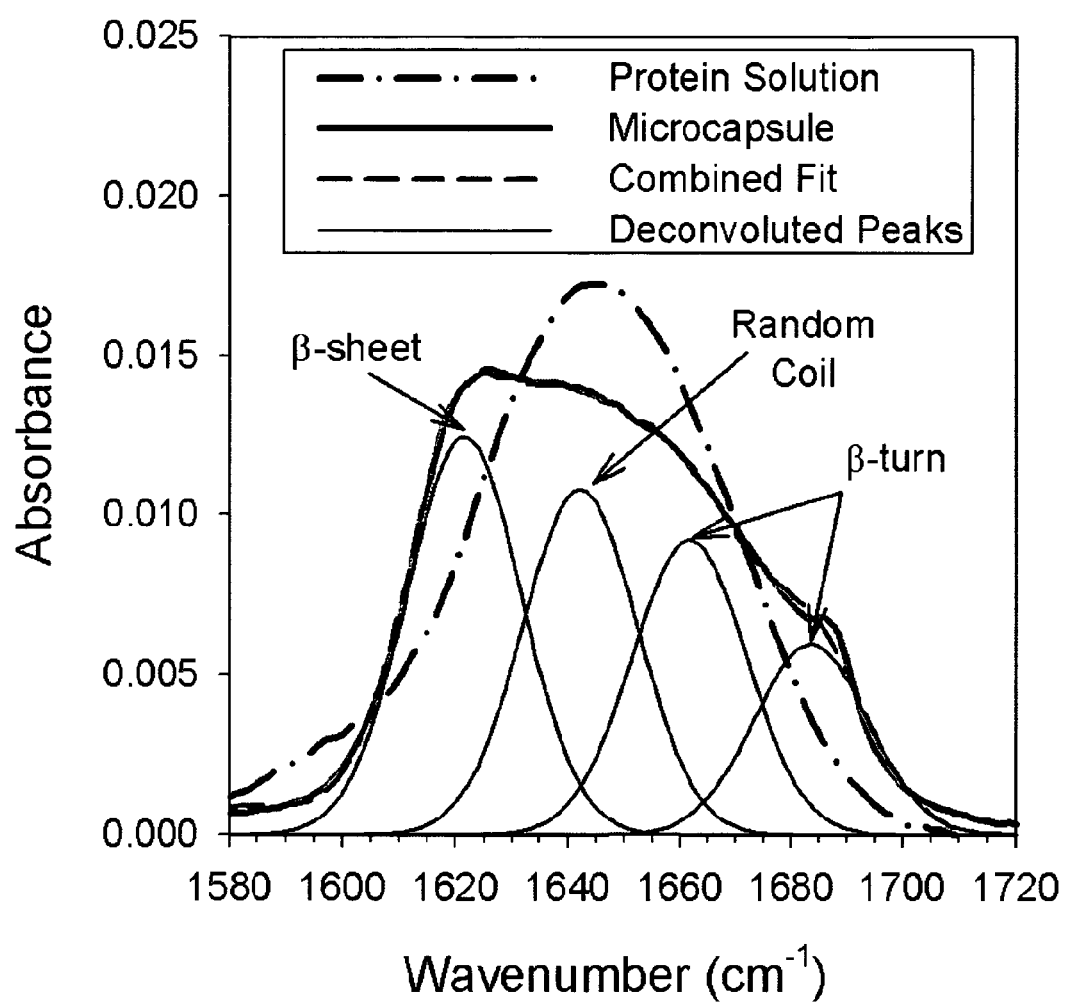

FIG. 6 IR spectra in $D_2O$ before (—·—·) and after (———) microcapsule formation. The shift in the spectra indicates a change in protein structure during microcapsule formation. Specifically, this shift indicates the formation of β-sheets. Deconvolution and Gaussian fit of microcapsule IR spectra reveals four peaks. Deconvoluted peaks are at 1621 $cm^{-1}$, 1642 $cm^{-1}$, 1661 $cm^{-1}$ and 1683 $cm^{-1}$ and are assigned respectively to β-sheets, random coil structures and two peaks for β-turns.

Figure 7:
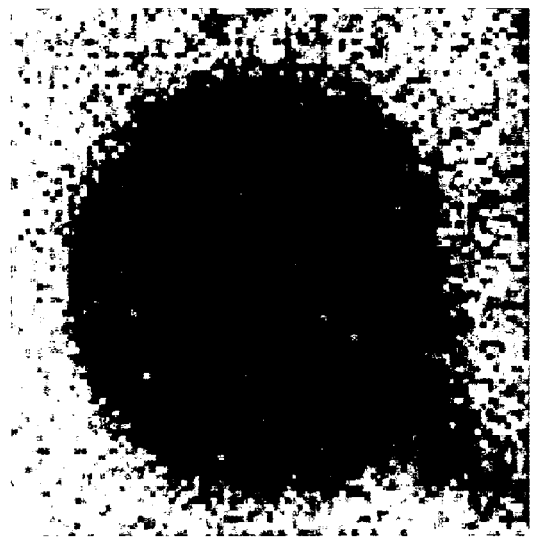
Figure 7:
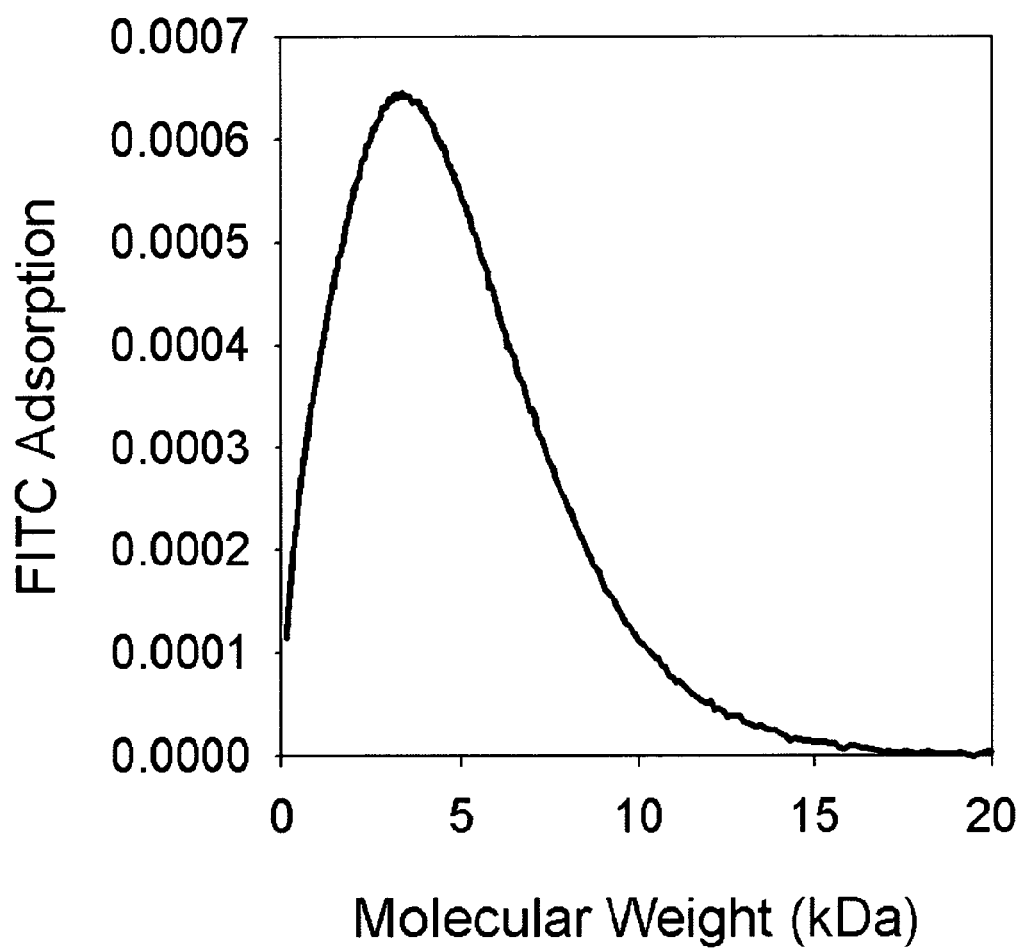
Figure 7:
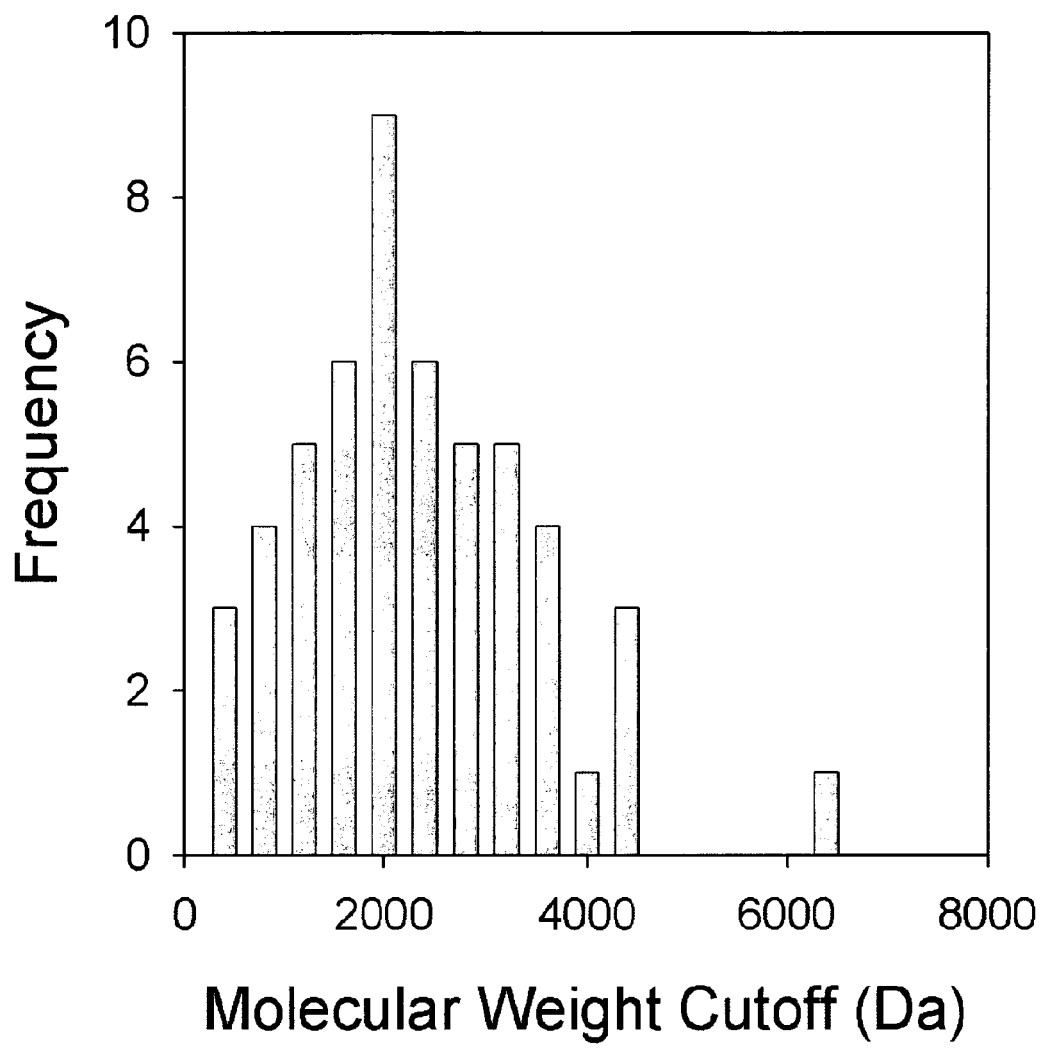

FIG. 7 Microcapsule permeability measurements. (A) Sample confocal image of a microcapsule in water with 0.3% 4 kDa FITC dextran added outside the microcapsule. A fraction of the dextran permeates the membrane. (B) Molecular weight distribution of dextran as measured by GPC fluorescence. (C) Measured molecular weight cutoff histogram for 51 microcapsules. Average molecular weight cutoff is 2.2 kDa.

Figure 8:
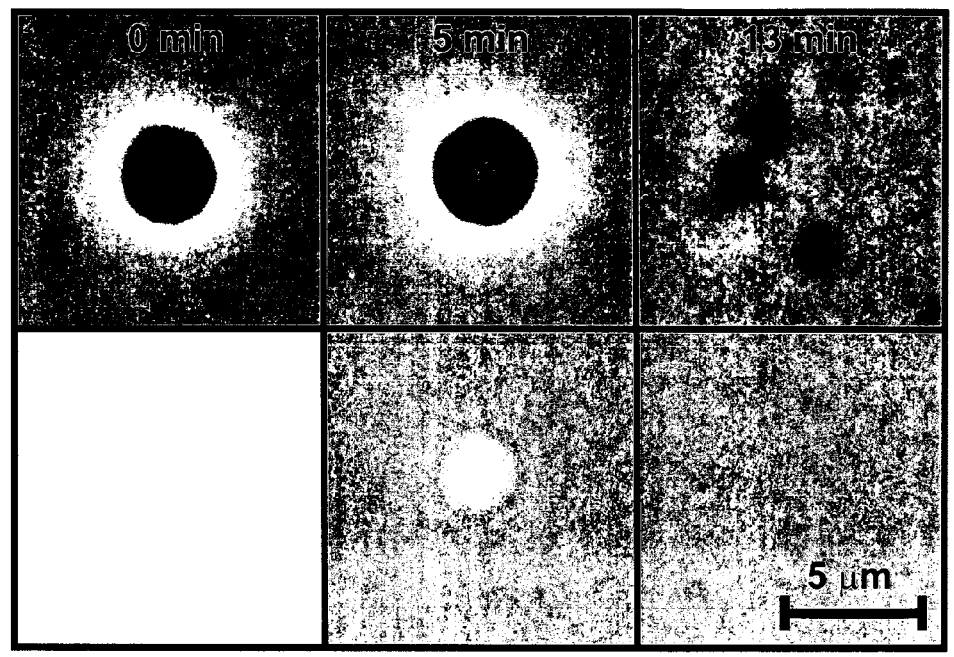

FIG. 8 Proteinase K digestion of $C_{16}$ microcapsules. Top row phase contrast image. Bottom row fluorescent image. As indicated by loss of fluorescence, dextran is released shortly after Proteinase K addition. Complete digestion of microcapsules occurs after 13±1 minutes.

Figure 9:
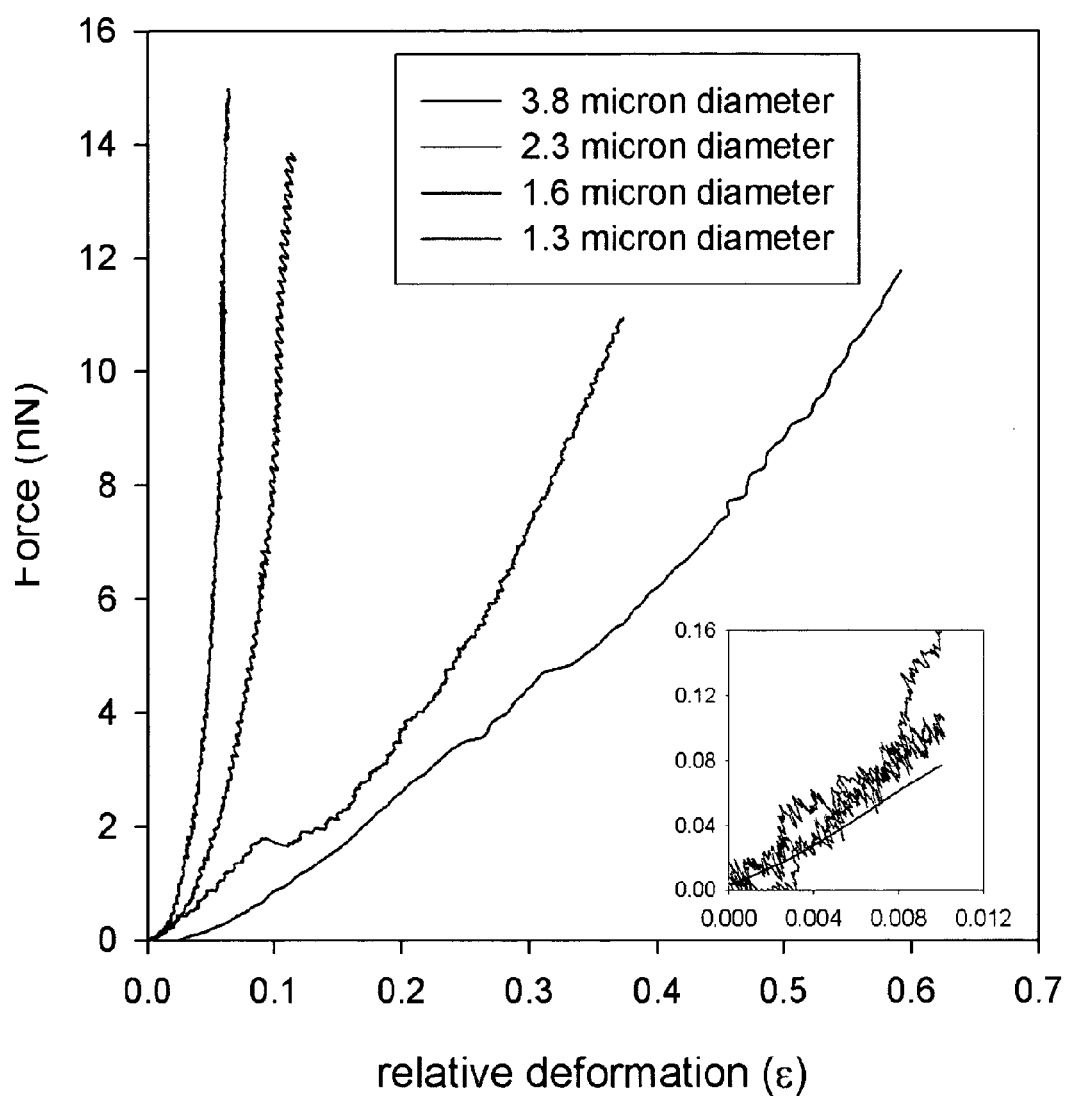

FIG. 9 Applied force versus microcapsule deformation as measured by AFM. Inset graph is the linear force regime during small deformations (ε<1%).

Figure 10:
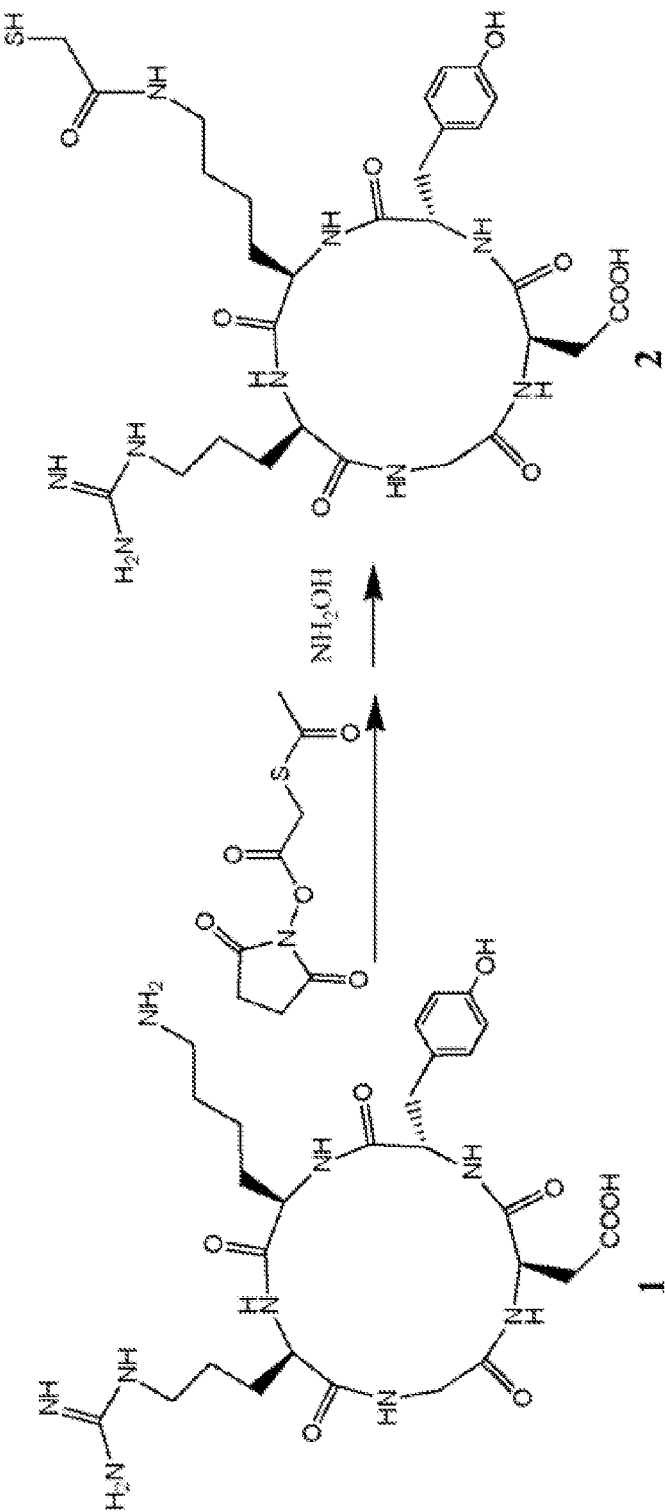
Figure 10:
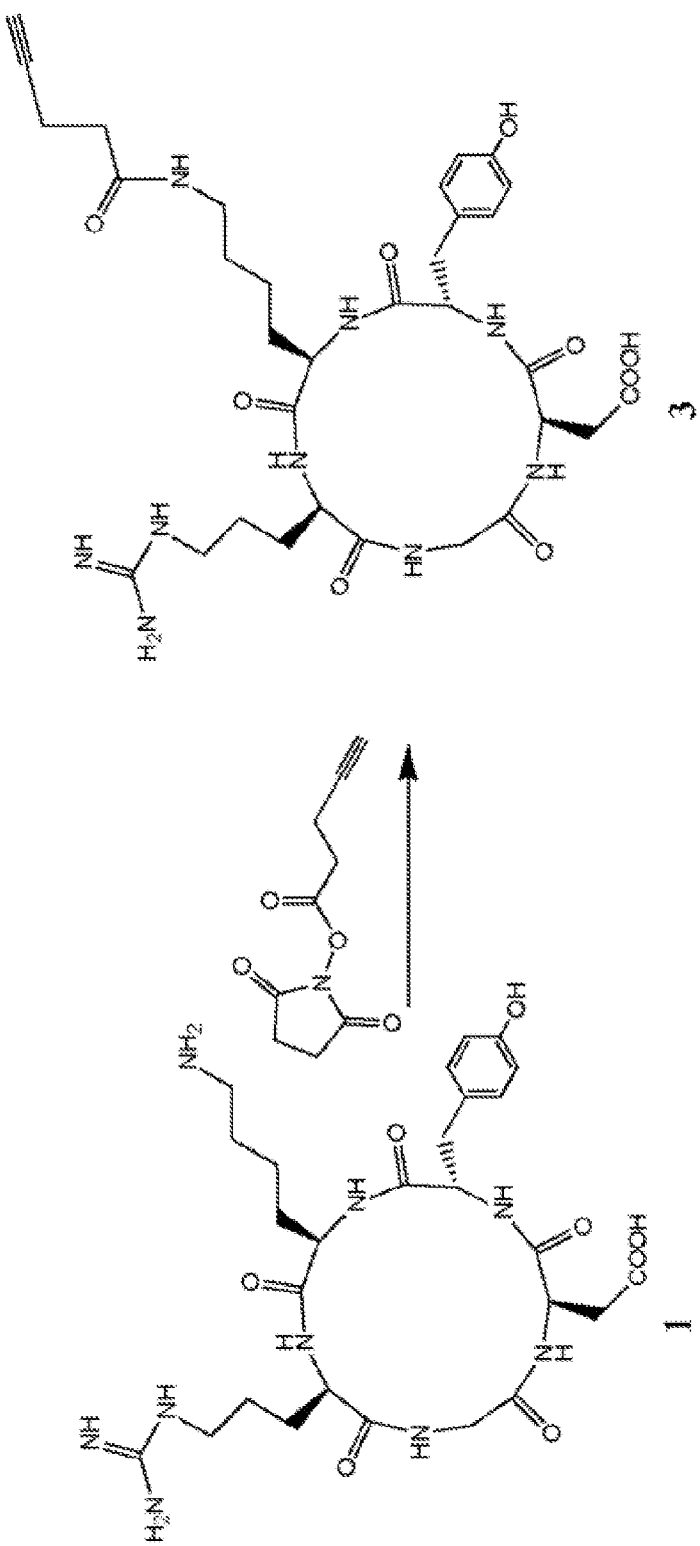

FIG. 10A and FIG. 10B illustrate the final steps in the synthesis of cyclic RGD molecules for use in the present invention.

EXAMPLES

Protein Preparation

The protein solution, from which the spider balloons were formed, was prepared by first dissolving recombinant spider dragline silk protein ($C_{16}$, see Huemmerich et al., 2004) at a concentration of 10 mg/ml in 6M guanidine thiocyanate. The protein solution was cooled to 4° C. and the concentration of guanidine thiocyanate was reduced below 1 mM by dialyzing the protein solution against a 10 mM Tris buffer, pH 8.0 overnight using dialysis tubing from Carl Roth GmbH with a molecular weight cutoff of 14 kDa. Any undispersed protein was removed by centrifuging the dialyzed solution for 30 minutes at a force of 100.000×g while maintaining the solution temperature at 4° C. The final protein concentration was determined using UV adsorption, employing the proteins extinction coefficient of 0.859 at a wavelength of 276 nm.

Microcapsule Formation

Figure 1:
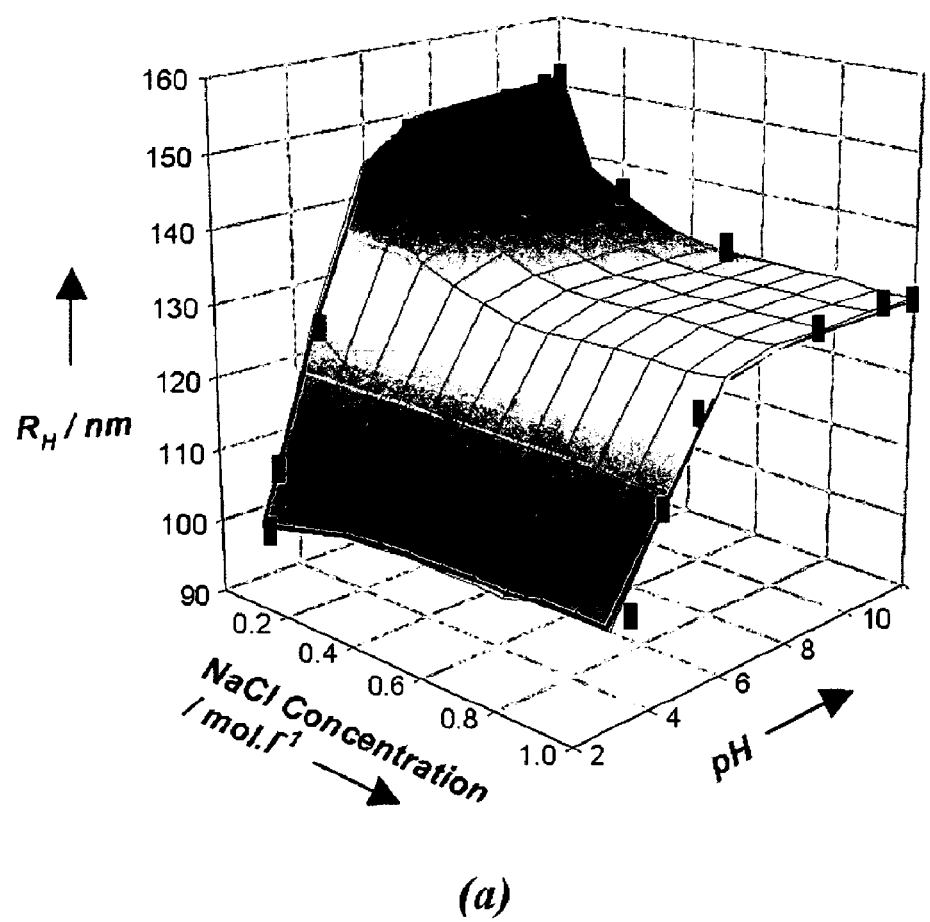
Figure 1:
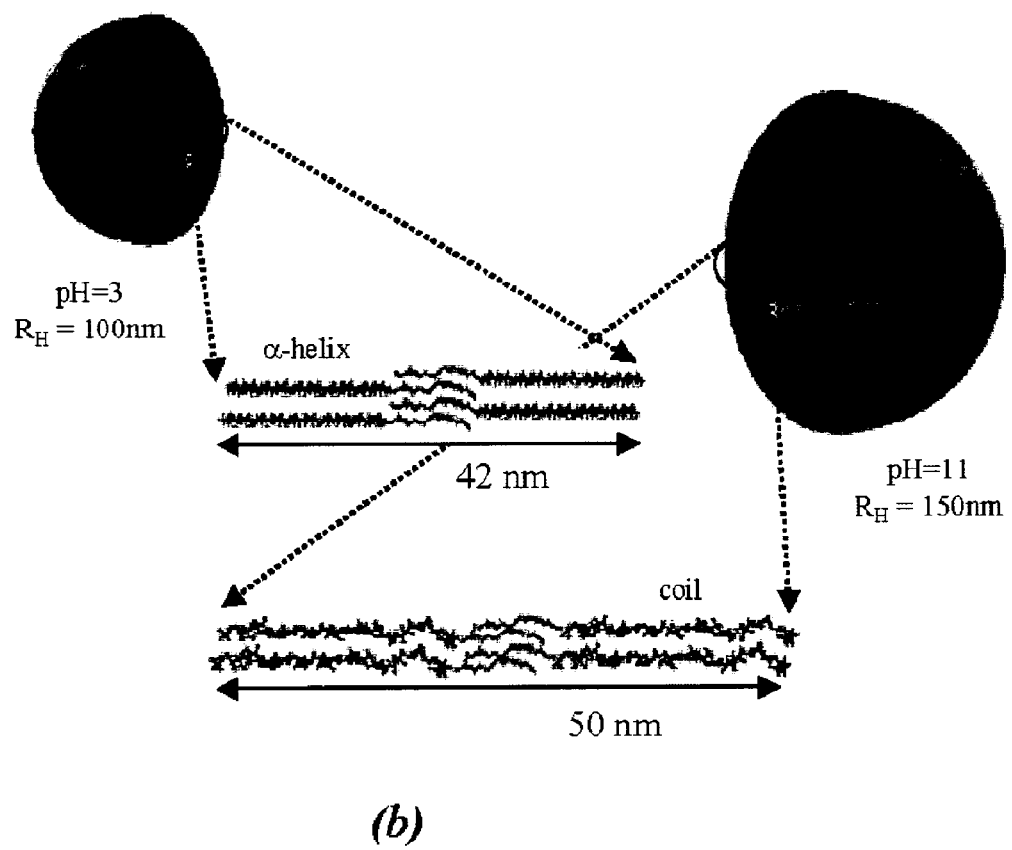
Figure 2:
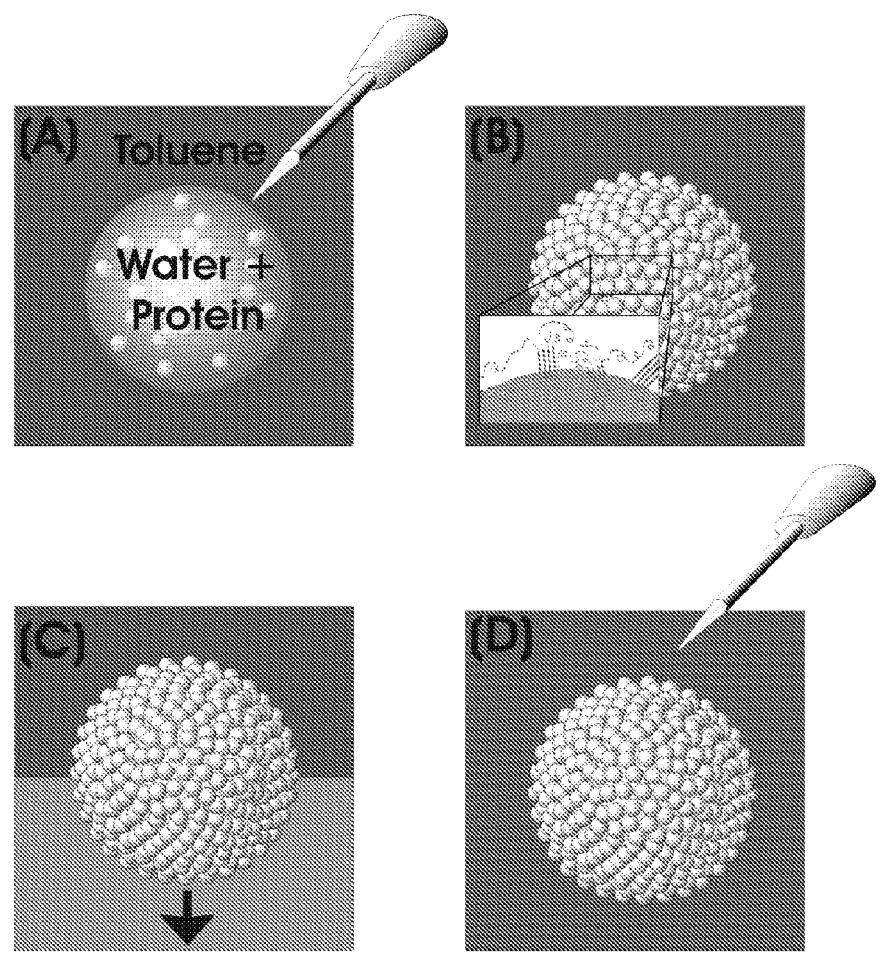

Microcapsules of spider silk were formed by emulsifying 5 µl of dialyzed protein suspension in 300 µl toluene for 90 seconds (FIG. 2A). During emulsification, silk protein adsorbs and changes its structural conformation at the surface of the emulsion droplets resulting in a polymer network that encapsulates the emulsion droplet (FIG. 2B). Spider silk microcapsules were formed using protein suspensions with concentrations ranging from 1 to 6 mg/ml and with emulsification times as short as 20 seconds. The size of the microcapsules formed depends on the size of the emulsion droplets.

Figure 3A:
FIG. 3 shows an image of spider bags/balloons in (A) toluene/ethanol (50:50) and (B) after transfer into water.
Figure 3:
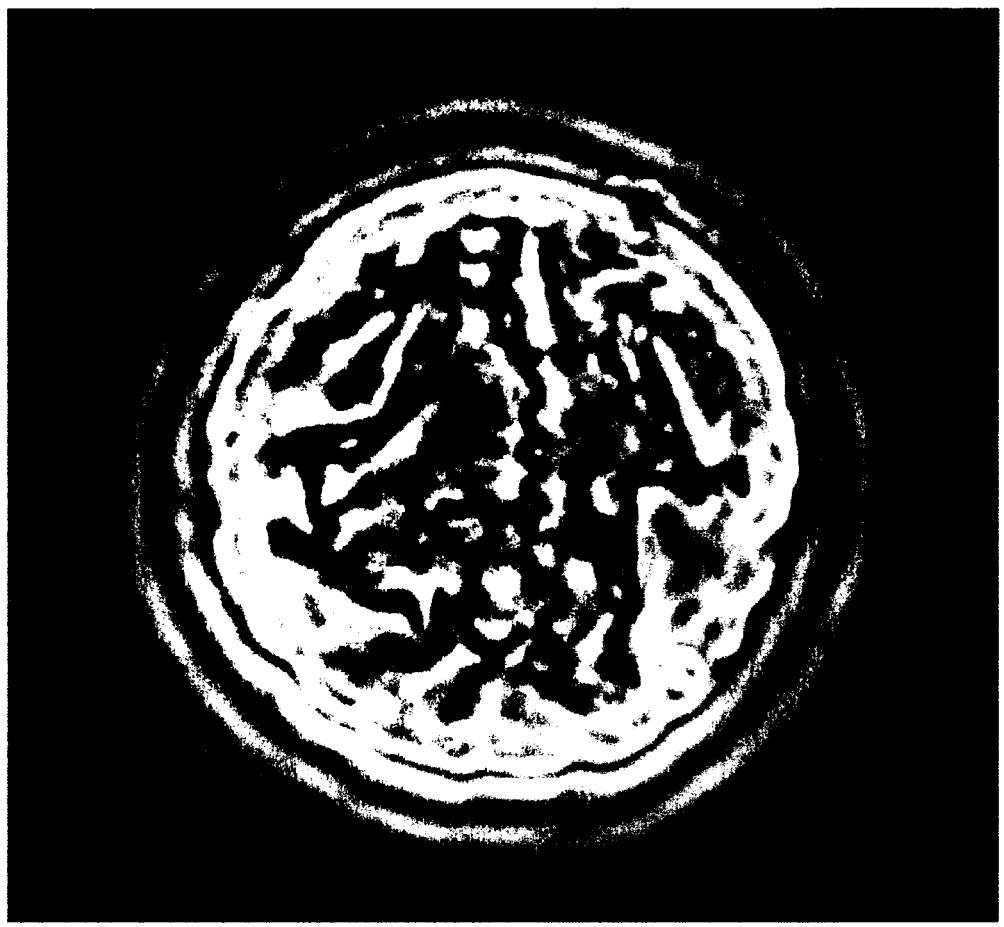

Once formed, the protein shells surrounding the emulsion droplets were transferred from the two-phase emulsion into a one-phase solution. Two different methods are effective in transferring the protein shells. In the first method, 300 µl of water was added to the toluene to form an aqueous sublayer. The protein shells surrounding the water droplets were centrifuged from the toluene layer into the aqueous sublayer at a force of 100×g for 4 minutes (FIG. 2C). In the second method, a one-phase solution was formed by adding 300 µl of ethanol to the two-phase emulsion, in order to solubilize the toluene and water (FIG. 2D). After using either method to transfer the microcapsules to a one-phase solution, the resulting structures were investigated with an optical microscope (FIG. 3).

Unlike soluble $C_{16}$, whose structure is primarily random coil, the assembled protein has a β-sheet-rich conformation. The change in $C_{16}$ conformation upon assembly was observed using IR microscopy. Initially, $C_{16}$ solubilized in $D_2O$ adsorbs at 1645 $cm^{-1}$, which is characteristic of proteins in a random coil structure (FIG. 6). After microcapsule formation two shoulders in the adsorption spectra emerge indicating a change in the secondary structure of $C_{16}$. Deconvolution of the spectra reveals the contribution of four Gaussian peaks at 1621 $cm^{-1}$, 1642 $cm^{-1}$, 1661 $cm^{-1}$ and 1683 $cm^{-1}$.

Figure 4:
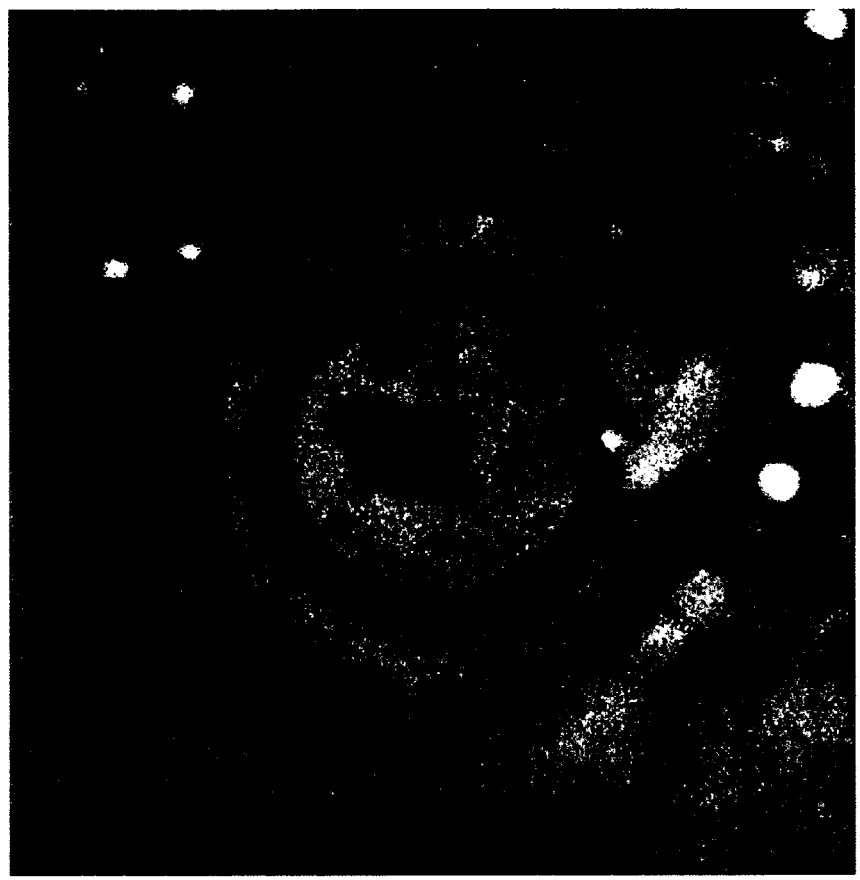
FIG. 4 is an image of spider bags/balloons filled with FITC-labeled Dextran (MW 500 kDa) after transfer into the continuous water phase: (A) bright field image. (B) fluorescent image.
Figure 4:
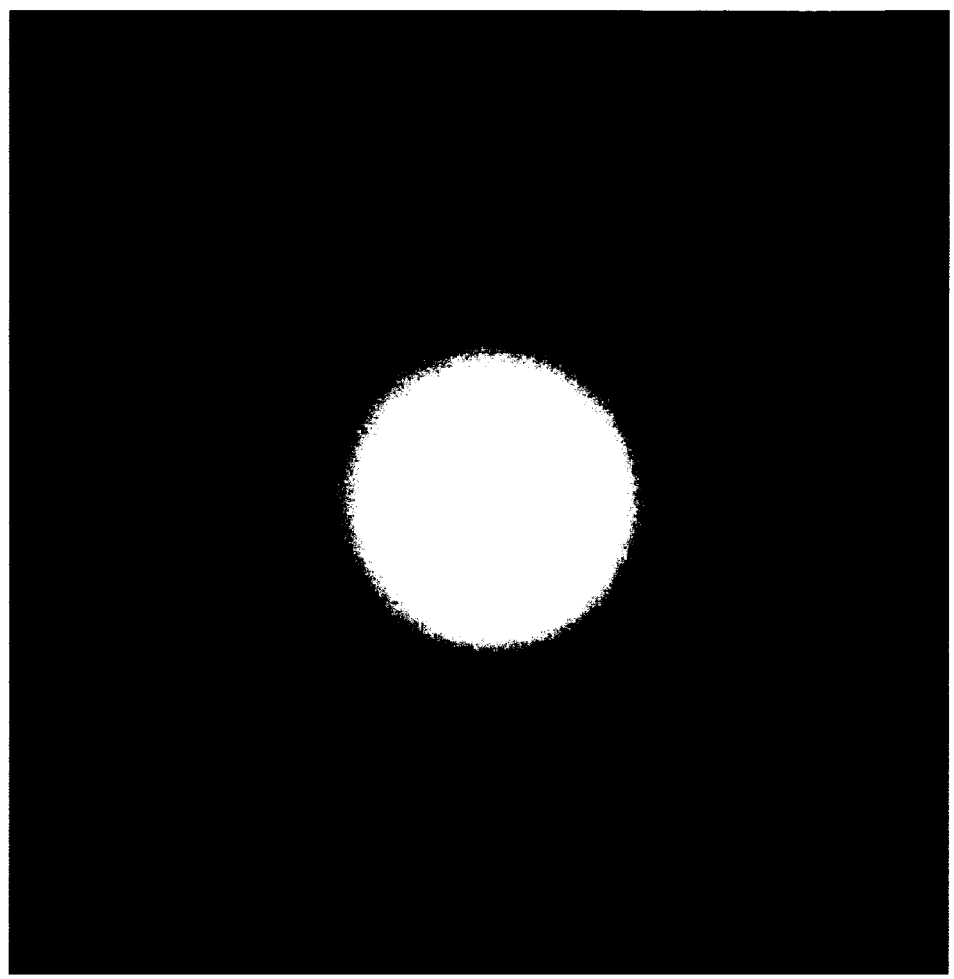
Figure 5:
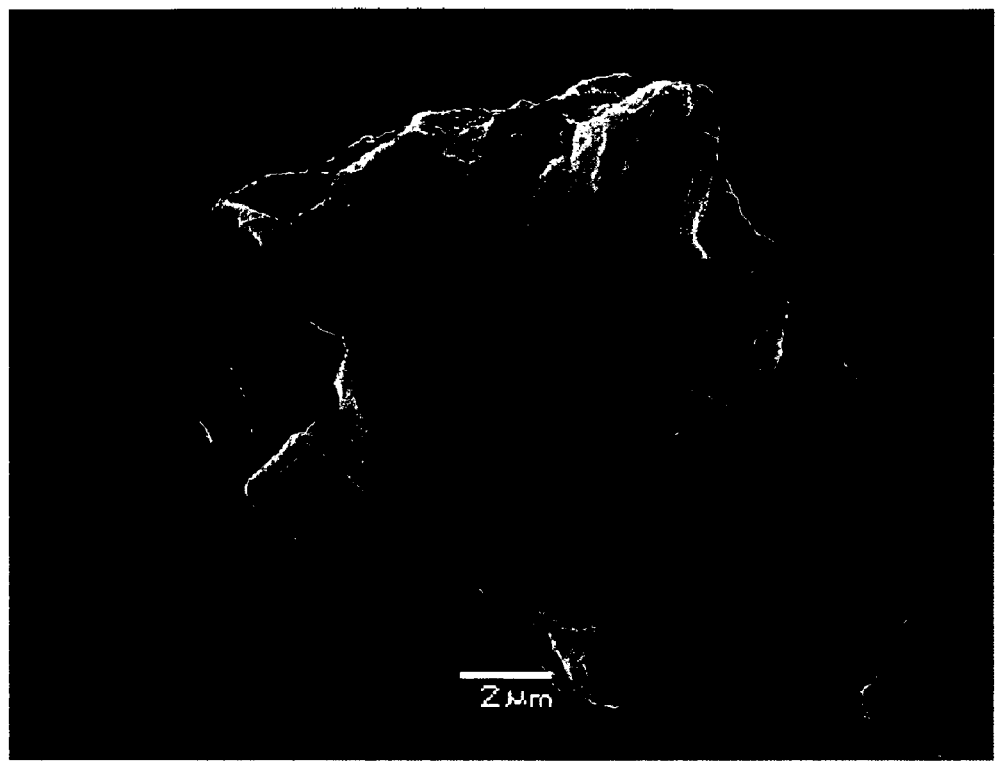
FIG. 5 shows dried Spider bags/balloons imaged by SEM. The membrane thickness has been determined to be smaller than 70 nm n.

The integrity of the centrifuged microcapsule-like protein shells was verified by adding 0.5 wt %, FITC labeled, 500 kDa Dextran (Sigma-Aldrich) to the protein solution prior to emulsification. After emulsification and centrifugation, the formed microcapsule-like structures continued to fluoresce indicating that the protein shell of these structures did not tear during centrifugation (FIG. 4). The microcapsule membrane can trap large molecules such as high molecular weight dextran but is permeable to small molecules such as fluorescein. If low molecular weight FITC labeled dextran is added to the outside of the centrifuged microcapsules a fraction of the dextran permeates the membranes and enters the capsules (FIG. 7A). The fractional admittance of the low molecular weight dextran occurs because the dextran has a non-finite polydispersity, comprising of both low and high dextran molecules (FIG. 7B). As a result the membrane admits the dextran below a certain molecular weight cutoff and excludes the dextran larger than this cutoff. By measuring the amount of fluorescence intensity inside the microcapsules and by using the fluorescent molecular weight distribution of the dextran (FIG. 7B) as measured by gel permeation chromatography, the molecular weight cutoff of the membrane was determined. The permeability of 52 different microcapsules in 13 different samples were measured. The molecular weight cutoff of these microcapsules ranged from 0.3 kDa to 6.0 kDa with an average molecular weight cutoff of 2.2 kDa ($r_g$~18 Å) (FIG. 7C).

Enzymatic triggered release of contents, such as FITC-labeled dextran, was demonstrated using the enzyme Proteinase K (FIG. 8). As indicated by the loss of fluorescence, shortly after the addition of Proteinase K the integrity of the microcapsule membrane is destroyed and the dextran is released. After the release of the dextran, the enzyme continues to digest the microcapsule until complete digestion occurs at 13±1 minutes.

The enzymatic digestion of the microcapsules can be prevented by chemically cross-linking $C_{16}$ through photo-initiated oxidation with ammonium peroxodisufate (APS) and Tris (2,2'-bipyridyl) dichlororuthenium (II) (Rubpy). To chemically crosslink the $C_{16}$, 10 mM APS and 100 mM Rubpy are added to the centrifuged solution, and the reaction is photo-initiated by exposing the mixture to light from a tungsten lamp for 5 minutes. This cross-linking renders the $C_{16}$ microcapsules stable against treatment with Proteinase K. After cross-linking, the addition of 100 μM Proteinase K to the crosslinked microcapsules has no effect on capsule integrity even after incubation for one hour at 37° C. This behavior is markedly different from the non-crosslinked microcapsules which release the encapsulated dextran almost immediately under the same conditions.

The formed microcapsules are observed to be highly elastic. The elasticity of the microcapsules was measured by compression with an AFM. For the compression measurements a 35 micron glass sphere attached to an AFM cantilever with a spring constant of 10 pN/nm and force versus deformation curves were obtained for microcapsules with sizes ranging from 1 to 4 microns (FIG. 9). At small deformations the relationship between the applied force, f, and the resultant deformation, ε, is described by $$f \propto Eh^2 \epsilon / \sqrt{12(1-\sigma^2)}$$

where h is the membrane thickness, E is the Young's modulus, σ is the Poisson ratio, and the pre-factor is a constant of an order of one. Using the maximum capsule wall thickness calculated from the initial concentration of silk monomer used and by assuming a Poisson ratio of 0.5, the microcapsules were determined to have a Young's modulus between E=0.7-3.6 GPa. The capsules also demonstrate excellent chemical stability. The addition of protein denaturants such as 2% sodium dodecylsulfate (SDS) and 8M urea has no effect on capsule integrity. The microcapsules were observed to be stable under these conditions for weeks.

REFERENCES

Chécot F, Lecommandoux S, Gnanou Y, Klok H A (2002), *Angew. Chem. Int. Ed.* 41, 1339

Chécot F, Lecommandoux S, Klok H A, Gnanou Y (2003) *Euro. Phys. J. E* 10, 25

Dinsmore A D, Hsu M F, Nikolaides M G, Marquez M, Bauscel A R, Weitz D A. (2002) *Colloidosomes: Selectively permeable capsules composed of colloidal particles. Science* 298(5595):1006-1009

Y. Y. Won, H. Davis, F. Bates, *Science* 283, 960 (1999)

Huemmerich D, Helsen C W, Quedzueweit S, Oschmann J, Rudolph R, Scheibel T (2004) *Primary structure elements of spider dragline silks and their contribution to protein solubility. Biochemistry* 43: 13604-12

Scheibel T (2004) *Spider silks: recombinant synthesis, assembly, spinning, and engineering of synthetic proteins, Microbial Cell Factories* 3, 14

---

The invention claimed is:

1. A method of producing nano- or microcapsules comprising the steps of:
   a) providing spider silk proteins,
   b) forming a solution or suspension of said proteins in a suitable solvent;
   c) generating an emulsion of at least two phases, said emulsion containing the solution or suspension formed in b) as a first phase and at least one further phase, which is substantially immiscible with said first phase,
   d) forming a polymer network of the spider silk proteins at the interface of the at least two phases,
   e) separating the protein polymer network generated in (d) from the emulsion.

2. The method of claim 1, wherein the spider silk proteins provided in a) are selected from the group of ADF-4, $C_{16}$, $C_{16}NR4$, $C_{32}$, and $C_{32}NR4$.

3. The method of claim 1, wherein the solvent in b) and/or the solvents of the at least one further phase is selected from the group consisting of hydrophilic solvents and lipophilic solvents.

4. The method of claim 1, wherein the emulsion formed in c) is of W/O, O/W, O/W/O or W/O/W type.

5. The method of claim 1, wherein the solvent used in b) further contains one or more pharmaceutical agents, cosmetical agents, foodstuffs or food additives.

6. The method of claim 5, wherein the pharmaceutical agent is present in the solvent in dissolved, suspended or solid form.

7. The method of claim 1, wherein the separation of the polymer network in step e) is done by means of centrifugation or by destroying the emulsion formed in step c) and forming a one-phase solution.

8. The method of claim 1, wherein the temperature used in steps b)-e) is 5-40° C. and wherein the pH used in steps b)-e) is 3-9.

9. The method of claim 1, wherein the size of the emulsion droplets and the nano- and microparticles derived therefrom is from 10 nm to 40 μm.

10. The method of claim 1, wherein the wall thickness of the obtained nano- and microcapsules is between 5 and 100 nm.

11. The method of claim 1, wherein the spider silk proteins provided in step a) are engineered in order to introduce protease specific recognition sequences allowing for tissue specific proteolysis.

12. The method of claim 1, wherein agents are coupled to the spider silk proteins before and after formation of the nano- or microcapsules in order to direct the capsules to specific cells or tissues.

13. The method of claim 12, wherein the agents are selected from RGD peptides which are cross-linked to the spider silk proteins, cell or tissue specific antibodies, cell or tissue specific receptors coupled to the spider silk proteins.

14. A nano- or microcapsule obtainable by the method of claim 1.

15. A pharmaceutical composition containing nano- or microcapsules of claim 14 and a pharmaceutically acceptable carrier.

16. A cosmetical or food product containing nano- or microcapsules of claim 14.

17. The method of claim 1, wherein the spider silk proteins provided in step a) comprise one or more of (AQ) and (QAQ) as repeat units.

18. The method of claim 17, wherein the spider silk proteins provided in step a) are selected from the group consisting of $(AQ)_{12}$, $(AQ)_{24}$, $(QAQ)_8$, and $(QAQ)_{16}$.

19. The method of claim 1, wherein the spider silk proteins comprise one or more synthetic repetitive sequences.

20. The method of claim 1, wherein the spider silk proteins comprise one or more authentic non-repetitive sequences.

* * * * *